US012149532B2

(12) United States Patent
Rieser et al.

(10) Patent No.: US 12,149,532 B2
(45) Date of Patent: Nov. 19, 2024

(54) DISTRIBUTED COMPUTATIONAL ANALYTIC SHARING ARCHITECTURE

(71) Applicant: The MITRE Corporation, McLean, VA (US)

(72) Inventors: Cj Rieser, McLean, VA (US); Robyn J. Wade, McLean, VA (US)

(73) Assignee: The MITRE Corporation, McLean, VA (US)

( * ) Notice: Subject to any disclaimer, the term of this patent is extended or adjusted under 35 U.S.C. 154(b) by 410 days.

(21) Appl. No.: 16/214,759

(22) Filed: Dec. 10, 2018

(65) Prior Publication Data

US 2019/0190921 A1   Jun. 20, 2019

Related U.S. Application Data

(60) Provisional application No. 62/620,944, filed on Jan. 23, 2018, provisional application No. 62/599,309, filed on Dec. 15, 2017.

(51) Int. Cl.

| H04L 9/40 | (2022.01) |
| G06F 16/903 | (2019.01) |
| G06F 21/62 | (2013.01) |
| G16H 40/20 | (2018.01) |
| G16H 70/40 | (2018.01) |
| H04L 67/025 | (2022.01) |

(Continued)

(52) U.S. Cl.
CPC ...... *H04L 63/102* (2013.01); *G06F 16/90335* (2019.01); *G06F 21/6245* (2013.01); *G16H 70/40* (2018.01); *H04L 63/0428* (2013.01); *H04L 63/08* (2013.01); *H04L 67/025* (2013.01); *H04L 67/10* (2013.01); *H04L 67/1097* (2013.01); *G06F 21/6263* (2013.01); *G16H 40/20* (2018.01)

(58) Field of Classification Search
None
See application file for complete search history.

(56) References Cited

U.S. PATENT DOCUMENTS

| 8,510,288 B2 * | 8/2013 | Mital | G06F 40/18 |
| | | | 707/708 |
| 2009/0180600 A1 * | 7/2009 | Blackwell | H04M 15/00 |
| | | | 379/114.28 |

(Continued)

*Primary Examiner* — Taghi T Arani
*Assistant Examiner* — Joshua Raymond White
(74) *Attorney, Agent, or Firm* — Morrison & Foerster LLP

(57) ABSTRACT

Described are systems and methods for securely distributing computational analysis across analytics nodes. In some embodiments, a system includes a plurality of analytics nodes with each analytics node managing access to its own data sources. The system includes an analytics controller configured to interact with a user to generate an analytic request including a selection of one or more analytics and a selection of one or more data sources determined based on the one or more selected analytics. The generated analytic request is transmitted to one or more analytics nodes corresponding to the one or more selected data sources. Each analytics node that receives the analytic request is configured to execute the analytic request to generate a result. The result from each analytics node of the one or more analytics nodes can be transmitted to the user issuing the analytic request.

17 Claims, 12 Drawing Sheets

(51) Int. Cl.
*H04L 67/10* (2022.01)
*H04L 67/1097* (2022.01)

(56) References Cited

U.S. PATENT DOCUMENTS

| | | | |
|---|---|---|---|
| 2010/0082240 A1* | 4/2010 | Short | G01C 21/387 |
| | | | 701/532 |
| 2012/0102074 A1* | 4/2012 | Mital | G06F 40/18 |
| | | | 707/805 |
| 2015/0186553 A1* | 7/2015 | Biehn | G06F 16/907 |
| | | | 707/708 |
| 2015/0200920 A1* | 7/2015 | Norton | H04L 63/0442 |
| | | | 713/153 |
| 2016/0004820 A1* | 1/2016 | Moore | G16H 15/00 |
| | | | 705/3 |
| 2017/0132277 A1* | 5/2017 | Hsiao | G06F 16/2425 |
| 2017/0286549 A1* | 10/2017 | Chandnani | G06F 16/81 |
| 2017/0300842 A1* | 10/2017 | Pembery | G06Q 10/0639 |
| 2018/0373419 A1* | 12/2018 | Chen | G06N 5/025 |
| 2019/0317949 A1* | 10/2019 | Florissi | G06F 16/27 |

* cited by examiner

DISTRIBUTED COMPUTATIONAL ANALYTIC SHARING ARCHITECTURE

CROSS REFERENCE TO RELATED APPLICATIONS

This application claims the benefit of U.S. Provisional Application Nos. 62/599,309, filed Dec. 15, 2017 and 62/620,944, filed on Jan. 23, 2018, each of which is herein incorporated by reference and for all purposes.

FIELD OF THE DISCLOSURE

This application relates generally to implementing a distributed computational analytic sharing architecture.

BACKGROUND OF THE DISCLOSURE

Many types of data include personally identifiable information or confidential information such as protected health information that needs to be carefully managed as required by law. For example, such data may include patient information maintained by a data server at a hospital. Currently, when a user (e.g., a scientist, a researcher, a doctor, etc.) wishes to perform analytics on the data, the user needs to request the dataset from one or more hospitals. Due to the stringent privacy laws, each hospital is required to sanitize its own data before providing the dataset to the user. Therefore, the user may not be able to perform desired analytics on the entire dataset.

Moreover, the hospital may be required to follow stringent protocols for transmitting the sanitized dataset to the user. As the number of user requests increases, the network bandwidth available to the hospital becomes more congested as the hospital needs to transmit the sanitized dataset to each user.

SUMMARY OF THE DISCLOSURE

To address the problems noted above, the disclosed embodiments describe a distributed computational analytic sharing architecture that enables each analytics node (e.g., a hospital data server) to manage access to its own local data store. Therefore, each analytics node can implement security and privacy policies specific to their data or as required by law. Then, instead of transferring the data containing sensitive information, an analytics controller in the computational analytic architecture can be configured to vet and transmit analytics to be performed on the data. As a result, the sensitive data in a local data store does not leave the purview of the analytics node, and the analytics node can be configured to vet or sanitize sensitive information from any generated results.

In some embodiments, a method for securely distributing computational analysis across analytics nodes includes: receiving a request from a user to issue an analytic request; providing the user with a plurality of analytics selected from an analytics registry based on matching a user access right of the user with user access requirements of analytics in the analytics registry; receiving, from the user, a selection of one or more analytics from the plurality of analytics; providing the user with a plurality of data sources selected from a data source registry based on the selection of the one or more analytics, wherein the plurality of data sources are associated with a plurality of analytics nodes; receiving, from the user, a selection of one or more data sources from the plurality of data sources; generating the analytic request, wherein the generated analytic request comprises the one or more analytics and the one or more data sources; transmitting the analytic request to at least one analytics node corresponding to the one or more data sources; and receiving a result from each of the one or more analytics nodes, the result indicating a result of executing the analytic request on a data source managed by a corresponding analytics node.

In some embodiments, the method includes: authenticating the user before providing the user with the plurality of analytics.

In some embodiments, receiving the selection of one or more analytics from the plurality of analytics includes: receiving an analytics flow combining two or more analytics selected from the plurality of analytics.

In some embodiments, providing the user with the one or more data sources selected from the data source registry includes: querying the analytics registry based on the selection of one or more analytics to determine input data requirements to each of the one or more analytics; and selecting each data source of the one or more data sources from the data source registry by matching the input data requirements with one or more data fields of each data source.

In some embodiments, the method includes: querying the data source registry for metadata associated with the selected one or more data sources to provide the user with an option to filter the data in the one or more data sources; receiving, from the user, data filter criteria entered by the user; and adding the data filter criteria to the analytic request.

In some embodiments, the method includes: encrypting the analytic request before transmitting; and signing the analytic request with a private key.

In some embodiments, transmitting the analytic request to the at least one analytics nodes corresponding to the one or more data sources includes: for a first data source of the one or more data source, querying the data source registry to identify a first analytics node of the at least one analytics nodes, wherein the first analytics node manages a local data store for storing the first data source.

In some embodiments, a method for securely distributing computational analysis across analytics nodes includes: at an analytics node coupled to a local datastore for storing one or more data sources: receiving an analytic request from an analytics controller, the analytic request indicating an analytic to be performed on the one or more data sources stored in the local datastore; vetting the analytic request to determine whether the analytic indicated in the analytic request is capable of being executed by the analytics node; upon determining that the analytic request can be executed, configuring an analytic zone to execute the analytic; retrieving the one or more data sources from the local datastore; executing the analytic on the one or more data sources in the analytic zone; storing a result of executing the analytic in a result file; and transmitting the result file to the analytics controller.

In some embodiments, the method includes: applying one or more software dependencies indicated in the analytic request to the analytic container.

In some embodiments, vetting the analytic request includes: querying an internal analytics registry to determine whether the analytic is stored.

In some embodiments, vetting the analytic request includes: vetting the analytic against privacy and software security requirements.

In some embodiments, the method includes: determining whether the result includes sensitive information; and in response to determining that the result includes sensitive information, sanitizing the result file of the sensitive information.

In some embodiments, the method includes: upon determining that the analytic request can be executed, adding the analytic request to a queue of analytic requests; and selecting the analytic request to be executed from the queue of analytic requests.

In some embodiments, a system for securely distributing computational analysis across analytics nodes includes one or more processors, memory, and one or more programs stored in the memory and configured to be executed by the one or more processors, the one or more programs including instructions for: receiving a request from a user to issue an analytic request; providing the user with a plurality of analytics selected from an analytics registry based on matching a user access right of the user with user access requirements of analytics in the analytics registry; receiving, from the user, a selection of one or more analytics from the plurality of analytics; providing the user with a plurality of data sources selected from a data source registry based on the selection of the one or more analytics, wherein the plurality of data sources are associated with a plurality of analytics nodes; receiving, from the user, a selection of one or more data sources from the plurality of data sources; generating the analytic request, wherein the generated analytic request comprises the one or more analytics and the one or more data sources; transmitting the analytic request to at least one analytics node corresponding to the one or more data sources; and receiving a result from each of the one or more analytics nodes, the result indicating a result of executing the analytic request on a data source managed by a corresponding analytics node.

In some embodiments, the instructions include: authenticating the user before providing the user with the plurality of analytics.

In some embodiments, receiving the selection of one or more analytics from the plurality of analytics includes: receiving an analytics flow combining two or more analytics selected from the plurality of analytics.

In some embodiments, providing the user with the one or more data sources selected from the data source registry includes: querying the analytics registry based on the selection of one or more analytics to determine input data requirements to each of the one or more analytics; and selecting each data source of the one or more data sources from the data source registry by matching the input data requirements with one or more data fields of each data source.

In some embodiments, the instructions include: querying the data source registry for metadata associated with the selected one or more data sources to provide the user with an option to filter the data in the one or more data sources; receiving, from the user, data filter criteria entered by the user; and adding the data filter criteria to the analytic request.

In some embodiments, the instructions include: encrypting the analytic request before transmitting; and signing the analytic request with a private key.

In some embodiments, transmitting the analytic request to the at least one analytics nodes corresponding to the one or more data sources includes: for a first data source of the one or more data source, querying the data source registry to identify a first analytics node of the at least one analytics nodes, wherein the first analytics node manages a local data store for storing the first data source.

In some embodiments, the system is a server.

In some embodiments, the system is a distributed cloud based system.

In some embodiments, a system for securely distributing computational analysis across analytics nodes includes: a local datastore configured to store one or more data sources; one or more processors, memory, and one or more programs stored in the memory and configured to be executed by the one or more processors, the one or more programs including instructions for: receiving an analytic request from an analytics controller, the analytic request indicating an analytic to be performed on the one or more data sources stored in the local datastore; vetting the analytic request to determine whether the analytic indicated in the analytic request is capable of being executed by the analytics node; upon determining that the analytic request can be executed, configuring an analytic zone to execute the analytic; retrieving the one or more data sources from the local datastore; executing the analytic on the one or more data sources in the analytic zone; storing a result of executing the analytic in a result file; and transmitting the result file to the analytics controller.

In some embodiments, the instructions include: applying one or more software dependencies indicated in the analytic request to the analytic container.

In some embodiments, vetting the analytic request includes: querying an internal analytics registry to determine whether the analytic is stored.

In some embodiments, vetting the analytic request includes: vetting the analytic against privacy and software security requirements.

In some embodiments, the instructions include: determining whether the result includes sensitive information; and in response to determining that the result includes sensitive information, sanitizing the result file of the sensitive information.

In some embodiments, the instructions include: upon determining that the analytic request can be executed, adding the analytic request to a queue of analytic requests; and selecting the analytic request to be executed from the queue of analytic requests.

In some embodiments, a non-transitory computer-readable storage medium includes instructions for securely distributing computational analysis across analytics nodes, wherein the instructions, when executed by a first cloud server having one or more processors, cause the one or more processors to perform instructions including: receiving a request from a user to issue an analytic request; providing the user with a plurality of analytics selected from an analytics registry based on matching a user access right of the user with user access requirements of analytics in the analytics registry; receiving, from the user, a selection of one or more analytics from the plurality of analytics; providing the user with a plurality of data sources selected from a data source registry based on the selection of the one or more analytics, wherein the plurality of data sources are associated with a plurality of analytics nodes; receiving, from the user, a selection of one or more data sources from the plurality of data sources; generating the analytic request, wherein the generated analytic request comprises the one or more analytics and the one or more data sources; transmitting the analytic request to at least one analytics node corresponding to the one or more data sources; and receiving a result from each of the one or more analytics nodes, the result indicating a result of executing the analytic request on a data source managed by a corresponding analytics node.

In some embodiments, a system for securely distributing computational analysis across analytics nodes includes: a plurality of analytics nodes with each analytics node configured to manage access to data sources stored in a local data store corresponding to the analytics node, wherein each analytics node includes: an internal data source registry configured to store metadata for each data source stored in the local data store, wherein the metadata includes information specifying types of data stored in the data source and user access requirements; an analytics repository configured to store analytics files that are vetted to satisfy privacy and software security policies; an internal analytics registry configured to store metadata of analytics corresponding to one or more of the analytics file determined to be compatible with at least one of the data sources registered in the internal data source registry; and an analytics processor configured to execute an analytic request received from an analytics controller by: determining whether an analytic included in the analytic request is stored in the internal analytics registry; building an analytic container to run the analytic on one or more data sources specified in the internal data registry; executing the analytic to generate a result; and transmitting the result to the analytics controller; and the analytics controller configured to manage user requests to perform analytics on one or more selected data sources, wherein the analytics controller includes: an external analytics registry configured to store metadata of analytics files stored by the plurality of analytics nodes; an external data source registry configured to store metadata stored in the internal data source registry of each analytics node of the plurality of analytics nodes; and an analytics dispatcher configured to: receive the analytic request entered by the user; transmit the analytic request to one or more analytics nodes corresponding to one or more data sources selected in the analytic request; and receive analytic execution results from the one or more analytics nodes.

In some embodiments, the analytics processor is configured to: determine whether the user that generated the analytic request is associated with user access rights that comply with the user access requirements associated with the one or more data sources.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the drawings.

DETAILED DESCRIPTION

Described herein are computer-readable storage mediums, systems, and methods for implementing a distributed computational analytic sharing architecture. In some embodiments, as will be further described below with respect to FIGS. 1A and 1B, the distributed computational analytic sharing architecture includes analytics nodes (e.g., a hospital data server) that each manages access to its own local data store. By managing access to and operations to be performed on its own local data store, each analytics node can implement security and privacy policies specific to their datasets or as required by law. The distributed computational analytic sharing architecture enables authorized users to add new data sources at each analytics node, as will be further described below with respect to FIG. 2A and FIGS. 3A-B.

In some embodiments, the types of analytic that may be performed on an analytic node's datasets may be dependent on the analytic node's security and privacy policies as well as the compatibility of the datasets and processing capability of the hardware and software of the analytics node. The distributed computational analytic sharing architecture enables authorized users to add new analytics that will be assessed and vetted by each analytics node, as will be further described below with respect to FIG. 2B and FIGS. 4A-B.

In some embodiments, to enable computational analysis to be distributed among the analytics nodes, an analytics controller in the computational analytic architecture can be configured to vet and distribute an analytic request to a portion of the analytics nodes having access to datasets corresponding to the analytic request, as will be further described below with respect to FIG. 2C and FIGS. 5A-B. Then, instead of transferring data containing sensitive information as may be required by traditional systems, an analytics node receiving the analytic request may be configured to perform the requested analytic on its dataset. Further, the analytics node may be configured to vet or sanitize sensitive information from any generated results before transmitting the results to a user that initiated the analytic request.

Figure 1A:
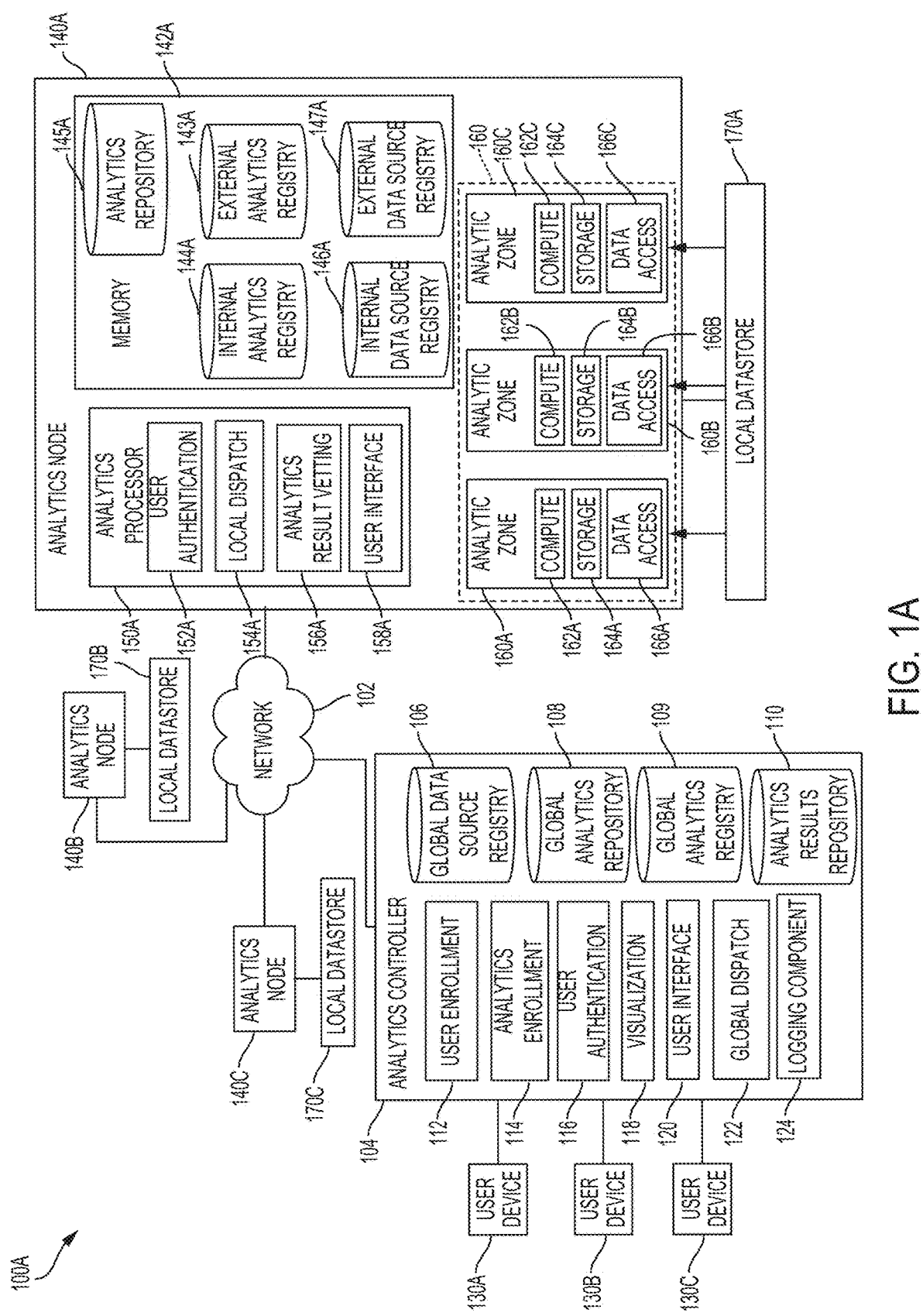
FIG. 1A illustrates a system that implements a distributed computational analytic sharing architecture, according to some embodiments.
Figure 1B:
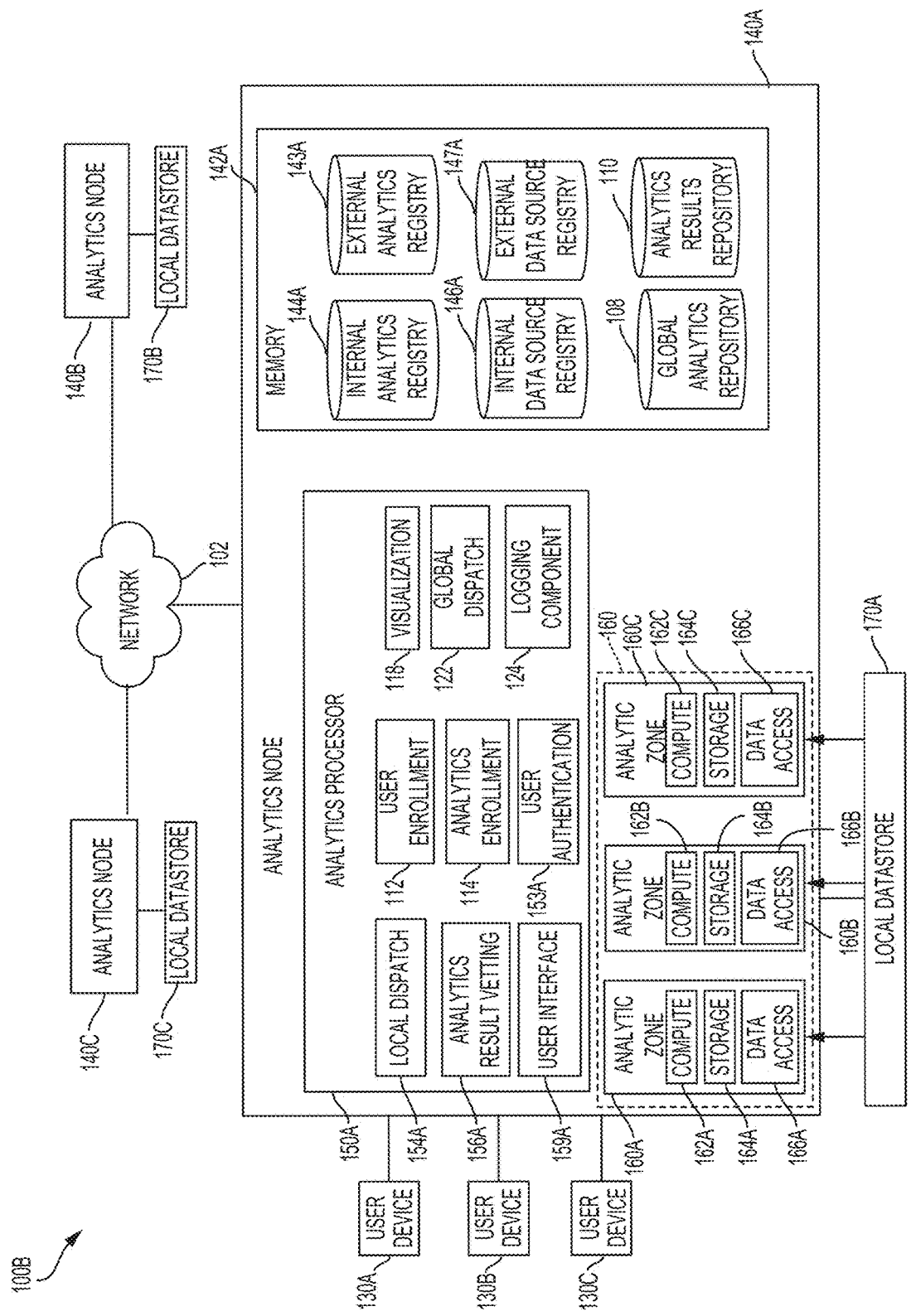
FIG. 1B illustrates a system that implements a distributed computational analytic sharing architecture, according to some embodiments.

FIGS. 1A and 1B illustrate example implementations of the distributed computational analytic sharing architecture, discussed above. FIGS.

FIG. 1A is a block diagram of a system 100A illustrating a distributed computational analytic sharing architecture, according to some embodiments. System 100A includes user devices 130A-C and a plurality of analytics nodes 140A-C that are communicatively coupled to an analytics controller 104 through network 102. As shown in FIG. 1A, the distributed computational analytic sharing architecture of system 100A can be configured as a centralized system (which may also be referred to as a "hub and spoke" system) having a central controller, i.e., analytics controller 104, that may coordinate computational analysis across two or more analytics nodes 140A-C based on an analytic request from any one of analytics nodes 140A-C or any one of user devices 130A-C.

Network 102 may include a local area network (LAN), a wide area network (WAN), the Internet, a Wi-Fi network, a WiMAX network, a cellular network (e.g., 3G, 4G, 4G Long Term Evolution (LTE)), or a combination thereof. Further, network 102 may implement one or more wired and/or wireless standards or protocols. In some embodiments, as will be further described below with respect to FIG. 1B, the analytics node and analytics controller can be hosted on the same network, on the same physical server, or wrapped in a single application instance.

In some embodiments, one or more of analytics controller 104 and analytics nodes 140A-C may be implemented in the "cloud." A "cloud" can include a network of remote servers hosted over network 102, such as the Internet, or on a private network that provides shared computer processing resources (e.g., computer networks, servers, data storage, applications, and services). For example, analytics node 140A may be provisioned within a cloud computing service such as Amazon Web Services (AWS), IBM SmartCloud, Microsoft Azure, Google Cloud Platform, etc.

In some embodiments, analytics controller 104 and each of analytics nodes 140A-C implement a secure message transport mechanism to securely exchange messages. A message may include instructions to dispatch an analytic request to one or more analytics nodes 140A-C. The message may include information to signal a status of an analytic request being processed. In some embodiments, a message may include a payload to provide means for a user to retrieve a result of an analytic executed on an analytics node. In some embodiments, the payload of the message may include an analytics file (e.g., an executable file or a source code file).

In some embodiments, the secure message transport mechanism may be to establish a virtual private network (VPN) tunnel between two entities (e.g., between analytics controller 104 and analytics node 140A) such that all communications between the two entities remain secure.

In some embodiments, the secure message transport mechanism may be secure email, remote procedure call (RPC) based inter-process communications, Hyper Text Transfer Protocol Secure (HTTPS), secure file transfer protocol (FTP), or the like. In some embodiments, the secure message transport mechanism includes encryption and sender authentication. For example, encryption and sender authentication may be implemented using a public key infrastructure (PKI) mechanism.

In some embodiments where the secure message transport mechanism is secure email, messages generated by an entity (e.g., analytics controller 104 or analytics node 140A) can be inserted in the body of an email. In some embodiments, these messages can be inserted into a file attached to the email.

In some embodiment, analytics controller 104 includes global data source registry 106, global analytics repository 108, global analytics registry 109, and analytics results repository 110.

Global data source registry 106 stores information (e.g., metadata) about each data source remotely stored and managed by each of analytics nodes 140A-C. For example, an analytics node such as analytics node 140A may add a data source entry in internal data source registry 146A and notify analytics controller 104 of the update. In response to receiving the update, analytics controller 104 can be configured to update global data source registry 106 to include information about the new data source entry added by analytics node 140A. In some embodiments, by managing a repository of the remote data sources, analytics controller 104 can query global data source registry 106 to identify data sources that are compatible for a given analytic requested by the user.

In some embodiments, similar to the concept of external analytics registry 143A in analytics node 140A, an analytics node may implement an external data source registry so that the local analytics node does not have to query analytics controller 104 for available data sources located remotely from the analytics node when a user wishes to dispatch an analytic request against those remotely-located data sources. For example, analytics node 140A may be configured to implement external data source registry 147A. Like internal data source registry 146A that stores metadata of data sources managed by the analytics node, external data source registry 147A may store metadata of data sources managed by other analytics nodes. Therefore, the user that interfaces with analytics node 140A may directly query external data source registry 147A for any remotely-located data sources. The remotely-located data sources may refer to data sources managed by other analytics nodes such as analytics nodes 140B or 140C. In effect, analytics node 140A may implement internal data source registry 146A and external data source registry 147A that together comprise a subset of global data source registry 106. In some embodiments, internal data source registry 146A and external data source registry 147A comprise the entirely of the information contained in global data source registry 106.

In some embodiments, a data source can be a data structure for storing a data set. For example, the data source may be a distributed file system, database, a file, a data sheet, a spreadsheet, an XML file, a text file, etc.

In some embodiments, global data source registry 106 stores one or more of the following metadata for each data source:

| METADATA | DESCRIPTION |
| --- | --- |
| Unique Identifier | |
| Name | Short descriptive name of the data source |
| Description | Brief description of the types of data in the data source |
| Storage Type | Local Disk, NAS, distributed file system, etc. |
| Storage Location | Information identifying where the data source is stored |
| Data Format | Format of data (e.g., CSV, WFDB, HDF5, MATLAB, etc.) |
| File Naming Convention | |
| Data Fields Available | Data fields of the dataset in the data source and an associated data type and format for each data field |
| User Privileges Required | Requirements for user access |
| Summary of data | Description of populations, min/max/avg values, etc. within the data set |

In some embodiments, storage location stored in global data source registry 106 may indicate a specific analytics node.

In some embodiments, analytics controller 104 may implement a data converter repository that stores a plurality of data conversion functions that can be retrieved by analytics controller 104 to convert a dataset in the data source to a specific format required by an analytic.

Global analytics repository 108 stores a plurality of analytics that have been vetted by analytics controller 104 against privacy and software security policies. In some embodiments, an analytic may be stored as a source code file. In other embodiments, the analytic may be stored as an executable file.

Global analytics registry 109 stores metadata associated with each analytic. In some embodiments, the metadata includes information needed by an analytics node to provision and execute the analytic on appropriately formatted data sources. For example, global analytics registry 109 may store one or more of the following metadata for each analytic stored in global analytics repository 108:

| METADATA | DESCRIPTION |
| --- | --- |
| Unique Identifier | |
| Analytic Name | Short descriptive name of the analytic (e.g. QRS detection) |
| Analytic Description | Brief description of what the analytic does |
| Version | |
| Link to Analytic | Identifies a location of where the analytic (e.g., an analytic executable) is stored |
| Operating Requirements | Minimum memory, minimum CPU, and storage requirements; Operating System Requirements (if any) |
| Software Dependencies | Software packages/versions required to run the analytic (e.g., MATLAB, specific Linux packages). If open-source dependencies exist, a link (e.g., a URL) to download the dependency may be included. |
| Input Parameters | For each parameter, the following may be specified: parameter name, description, value type expected, allowable values, required/optional indicator |
| Input Data Format | Format of data to be read by the analytic (e.g. CSV, WFDB, HDF5, MATLAB) |
| Input Data Fields Required | Data fields/value types required by the analytic |
| Output Data Format | Format of output data to be written by the analytic (e.g. CSV, WFDB, HDF5, MATLAB) |
| Output Data Fields | Data fields/value types generated by the analytic |

Analytics results repository 110 stores execution results of each analytic request. In some embodiments, an execution result may include results provided by two or more of analytics nodes 140A-C depending on which data sources are selected by the user, as will be further described with respect to FIGS. 5A-B. In some embodiments, an execution result may include a link (e.g., a web link) to access a result generated by an analytics node, such as analytics node 140A. In some embodiments, the user that issued the analytic request corresponding to a stored execution result may add user access requirements that enables certain users to access the execution result.

In some embodiments, analytics controller 104 can enable users operating user devices 130A-C to issue analytic requests that analytics controller 104 securely distributes across one or more analytics nodes 140A-C to perform requested analytics on data sources stored in local datastores 170A-C. In some embodiments, to provide such functionality, analytics controller 104 can be configured to implement the following components: user enrollment 112, analytics enrollment 114, user authentication 116, visualization 118, user interface 120, global dispatch 122, and logging component 124.

User enrollment 112 enables one or more of analytics nodes 140A-C and one or more users to be registered in the distributed computational sharing architecture. In some embodiments, by registering analytics nodes 140A-C, analytics controller 104 can be configured to securely communicate messages with each analytics node 140A-C to enable users to request analytics to be performed on one or more data sources managed by analytics node 140A-C.

Figure 4A:
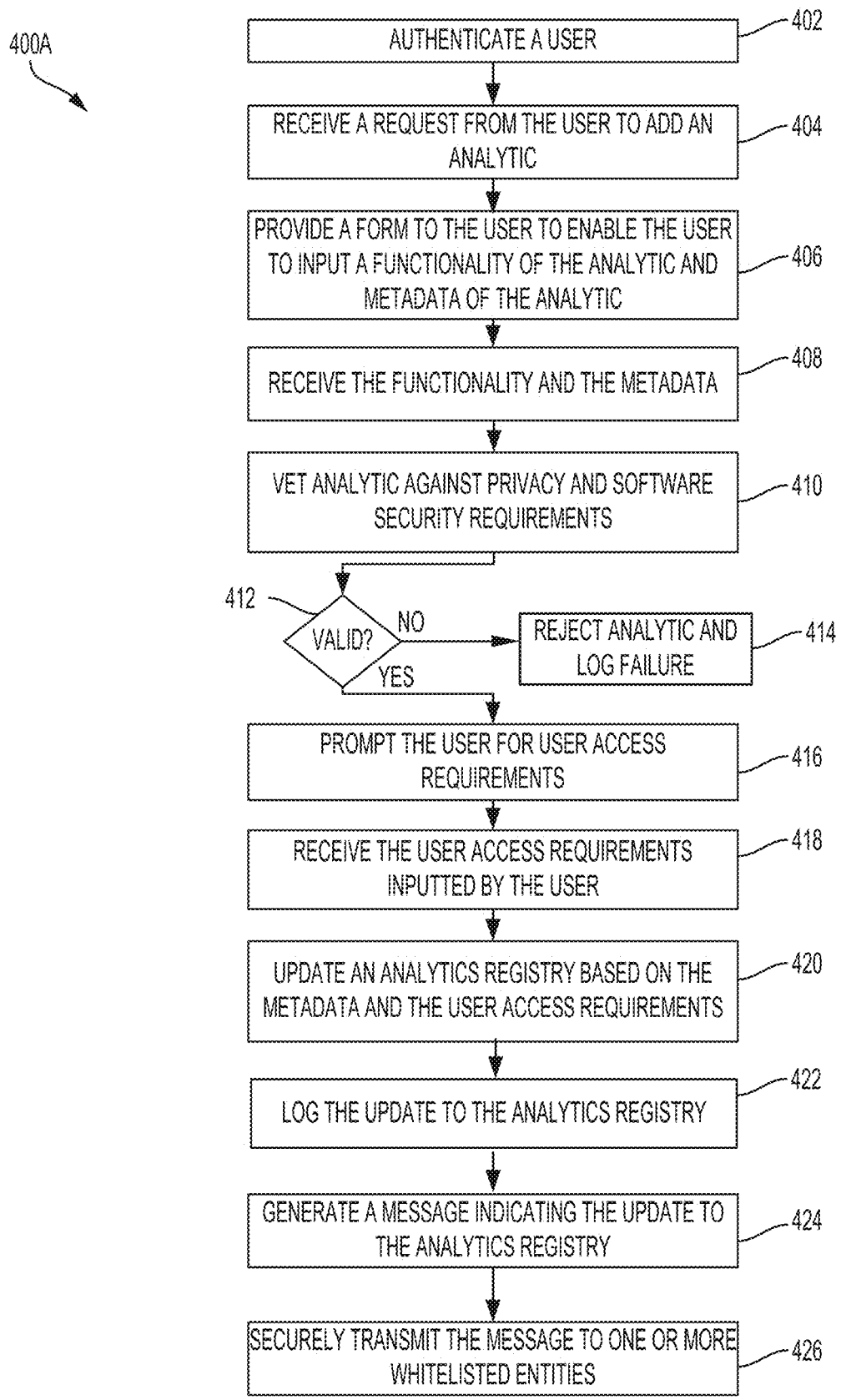
FIG. 4A illustrate a method that enables a user to add an analytic in a distributed computational analytic sharing architecture, according to some embodiments.
Figure 4B:
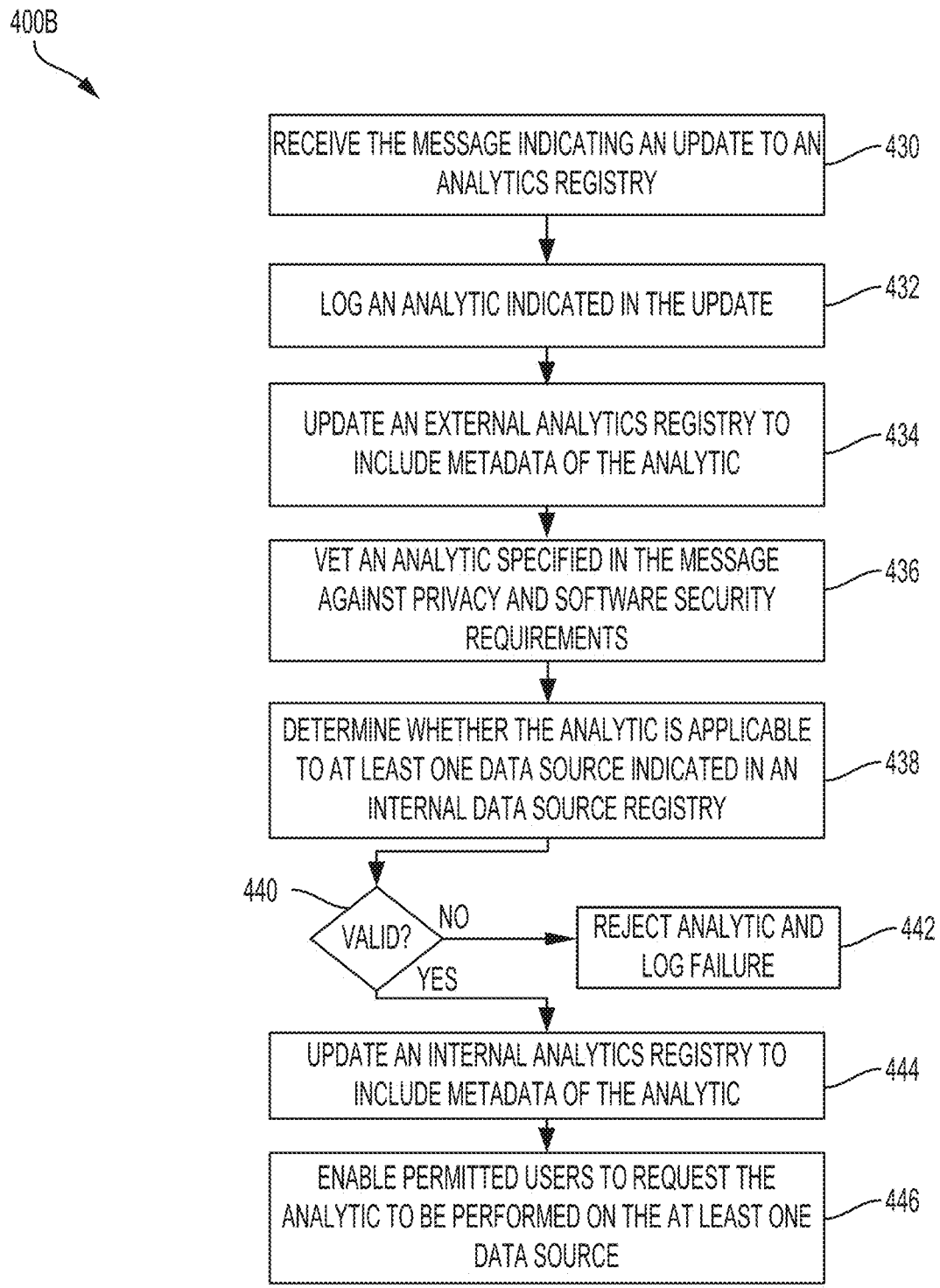
FIG. 4B illustrate a method for receiving and processing vetted analytics, according to some embodiments.

Analytics enrollment 114 enables a user operating a user device, e.g., user device 130A, to add new analytics to system 100A, as will be further described with respect to FIGS. 4A-B. In some embodiments, the user may upload an analytic file (e.g., a source code file or an executable file) storing the analytic. Before adding the analytic to global analytics repository 108, analytics enrollment 114 can be configured to vet the analytic file against privacy and software security requirement policies stored at analytics controller 104. For example, analytics enrollment 114 may run the analytic file in an isolated environment, e.g., a sandbox, to determine whether the analytics file includes any malicious code. Additionally, analytics enrollment 114 may run one or more anti-malware software on the analytics file. In some embodiments, analytics enrollment 114 may determine whether a data type of an output of the analytic violates privacy requirements.

Figure 5A:
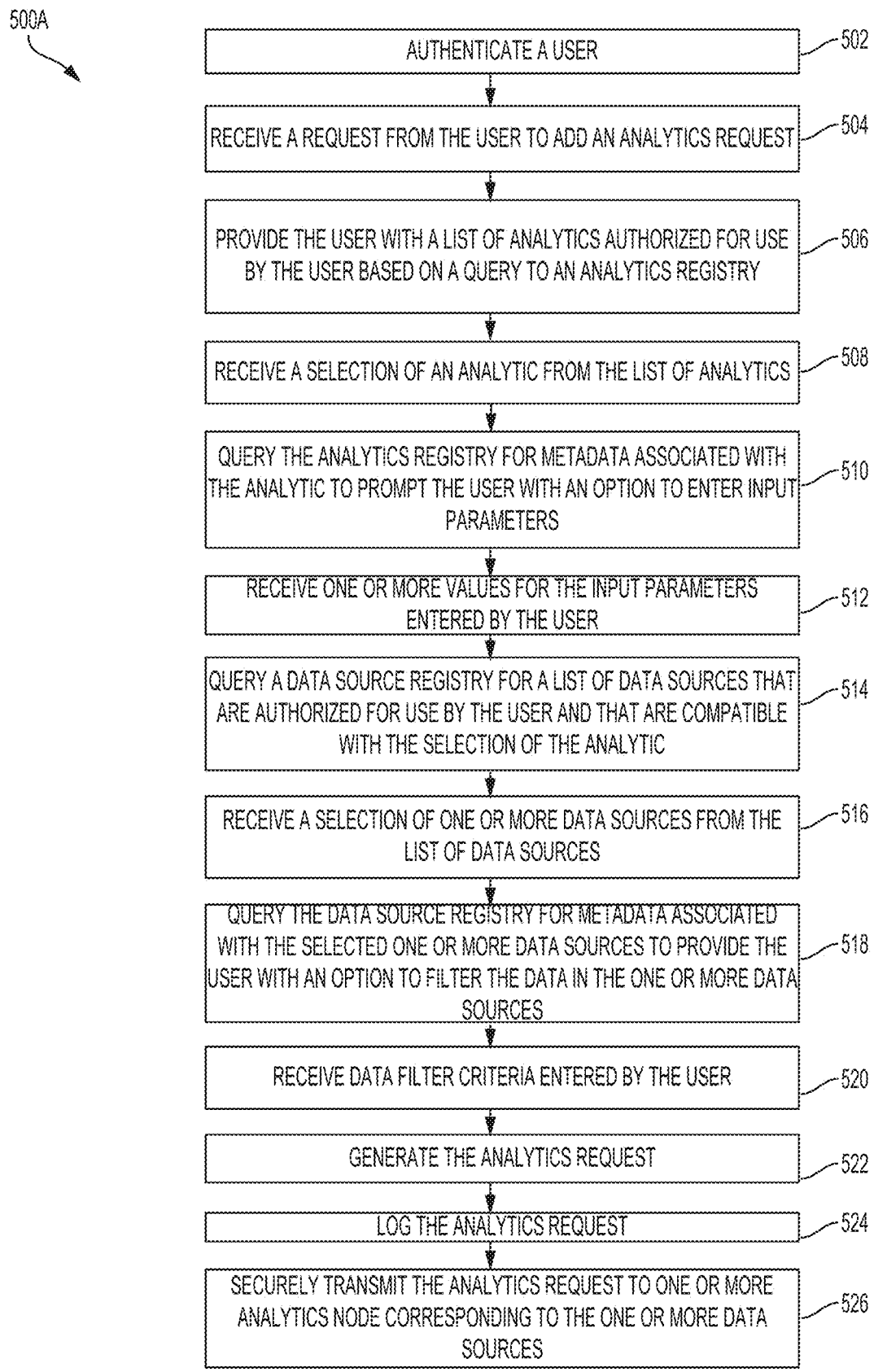
FIG. 5A illustrate a method that enables a user to issue an analytic request in a distributed computational analytic sharing architecture, according to some embodiments.
Figure 5B:
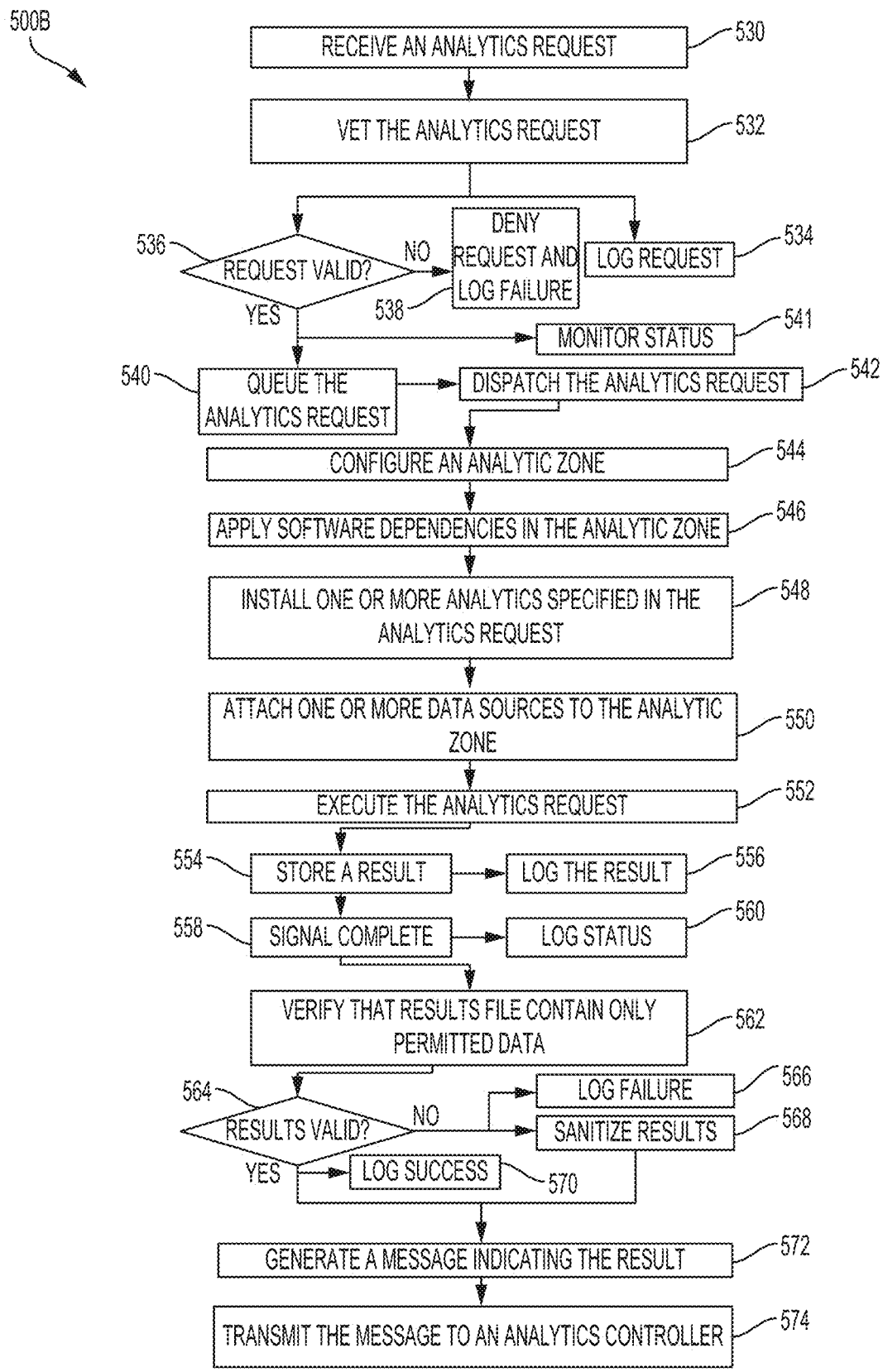
FIG. 5B illustrate a method for receiving and processing an analytic request, according to some embodiments.

Global dispatch 122 enables the user to submit an analytic request to be distributed to one or more analytics nodes 140A-C, as will be further described with respect to FIGS. 5A-B. In some embodiments, global dispatch 122 queries global analytics registry 109 to identify one or more analytics that the user can include in the analytic request. Based on the user's selection of an analytic, global dispatch 122 may query global data source registry 106 to identify one or more data sources that are compatible with the selected analytic. Then, global dispatch 122 may prompt the user to select one or more of the identified data sources.

In some embodiments, based on the user's selection of the analytic and one or more data sources, global dispatch 122 can be configured to generate the analytic request. In some embodiments, the analytic request includes a plurality of commands needed by an analytics node to build an analytic zone, install the analytic in the analytic zone, connect the analytic zone to one or more data sources, execute the analytic, signal a completion of the execution, and store a result of the execution. In some embodiments, commands associated with building the analytic zone may include commands to configure the analytic zone to comport with operating requirements specified in global analytics registry 109 for that analytic. In some embodiments, commands associated with installing the analytic zone may include commands to install one or more software dependencies specified in global analytics registry 109 for that analytic.

In some embodiments, based on the data sources selected by the user, global dispatch 122 may identify which of analytics nodes 140A-C to forward the analytic request. Accordingly, the analytic request may be distributed across multiple analytics nodes 140A-C.

In some embodiments, upon transmitting the analytic request to one or more analytics nodes 140A-C, global dispatch 122 can be configured to monitor a status of the analytic request being processed by each of the one or more analytics nodes 140A-C. For example, the status may be in progress, executing, completed execution, etc.

Visualization 118 can be configured to graphically depict results received by global dispatch 122. In some embodiments, visualization 118 enables the user to select different types of charts to display the results.

User authentication 116 authenticates the user before enabling user interface 120 to provide the graphical user interface to the user. For example, analytics controller 104 may request the user to enter a username and a password to access the various functionalities provided by analytics controller 104.

User interface 120 provides a graphical user interface to the user to allow the user to access the functionalities provided by one or more of analytics enrollment 114, global dispatch 122, and visualization 118. In some embodiments, the user may access the user interface by accessing a web page via, for example, a web browser.

In some embodiments, user interface 120 can be configured to provide a graphical user interface that selectively displays data or provided functionality based on a role or privileges associated with the user. For example, user authentication 116 may receive a user identifier (e.g., a username) as part of user authentication discussed above. User interface 120 may query a plurality of user profiles to identify the user profile corresponding to the user identifier. The user profile may include the user's role (e.g., an administrator, a PhD student, a doctor, etc.) and privileges.

In some embodiments, user interface 120 selectively displays within the graphical user interface graphical representations for one or more of the functionalities of analytics enrollment 114, visualization 118, or global dispatch 122 based on the privileges associated with the user. For example, the user may be a student at a university who may possess only privileges to access the computational analysis performed by one or more analytics nodes 140A-C. So, user interface 120 may graphically present the user with the option to submit analytic request (via global dispatch 122), but user interface 120 may omit the option for the user to, for example, enter his own analytics (via analytics enrollment 114).

Logging component 124 can be configured to log user activity, including requests to add analytics or analytic requests.

In some embodiments, analytics nodes 140A-C manage access to data sources stored on respective local datastores 170A-C. For example, each of analytics nodes 140A-C may be a hospital data server that maintains and manages access to patient data gathered at that hospital. The components displayed within analytics node 140A may be exemplary of the components implemented by each of nodes 140B-C.

In some embodiments, within memory 142A, analytics node 140A implements internal analytics registry 144A, external analytics registry 143A, internal data source registry 146A, and analytics repository 145A. In some embodiments, within memory 142A, analytics node 140A may also implement external data source registry 147A.

In some embodiments, internal data source registry 146A includes information associated with data sources accessible by analytics node 140A. In particular, these data sources may be stored in local datastore 170A coupled to analytics node 140A. In some embodiments, the information includes the metadata of a data source, as described above with respect to global data source registry 106. Additionally, the metadata may include a storage location that indicates where the data source is stored in local datastore 170A.

Analytics repository 145A may be a repository mirror (i.e., a local copy) of global analytics repository 108 maintained by analytics controller 104. In some embodiments, analytics node 140A synchronizes analytics repository 145A with global analytics repository 108. By storing a copy of analytics files, network bandwidth between analytics node 140A and analytics controller 104 can be reduced since an analytic file storing the analytic need only be transmitted once from analytics controller 104. In some embodiments, analytics processor 150A can be configured to synchronize analytics repository 145A with global analytics repository 108. In some embodiments, analytics processor 150A can perform the synchronization periodically or upon receiving an update from analytics controller 104.

External analytics registry 143A may store information (e.g., metadata) of analytics stored in analytics repository 145A. As will be described below, external analytics registry 143A may store analytics that have been vetted and permitted for use by analytics node 140A regardless of whether analytics node 140A has access to the types of data required by the analytic.

In contrast, internal analytics registry 144A may store information (e.g., metadata) of analytics that analytics node 140A has determined is applicable to one or more data sources stored in local datastore 170A. In some embodiments, analytics node 140A may only store the information of the analytic upon determining that analytics node 140A meets the operating requirements specified by the analytic. As will be described with respect to FIG. 5A, a user wishing to submit an analytic request for execution may be presented with a list of analytics available to that user, including those in external analytics registry 143 A and/or internal analytics registry 144A.

In some embodiments, analytics node 140A includes analytics processor 150A to implement one or more of the following components: user authentication 152A, local dispatch 154A, analytics result vetting 156A, and user interface 158A.

User interface 158A can be configured to provide a user with a graphical user interface (GUI) to add a new data source, as will be further described below with respect to FIGS. 2A and 3A-B. In some embodiments where functionality of analytics controller 104 is implemented within analytics node 140A, as will be described with respect to FIG. 1B below, user interface 158A can be additionally configured to provide the user with a GUI to add a new analytic and execute an analytic, as will be further described with respect to FIGS. 2B, 2C, 4A, 4B, 5A, and 5B. For example, user interface 158A may provide the graphical user interface within a web page that the user can access through, for example, a web browser.

In some embodiments, like user interface 120, user interface 158A may be configured based on the user's role or privileges to selectively display, within the graphical user interface, graphical options that enable the user to access a limited number of the functionalities of analytics controller 104 and analytics node 140A. For example, based on the user's role or privileges, user interface 158A may be configured to omit one or more of the following functionalities: adding or removing an analytic via analytics enrollment 114, adding or removing a new dataset, submitting an analytic request via global dispatch 122 and local dispatch 154A, access to specific data sources or sub-fields of data sources when generating the analytic request, or visualizing results of computational analysis via visualization 118, etc.

User authentication 152A can be configured to authenticate the user before allowing the user to access user interface 158A by requesting the user to provide a username and a corresponding password.

Local dispatch 154A can be configured to process analytic requests from analytics controller 104. In some embodiments, as will be further described with respect to FIGS. 5A-B, local dispatch 154A can queue a plurality of analytic requests. In some embodiments, to concurrently execute a plurality of analytic requests, local dispatch 154A can configure an analytic zone (e.g., analytic zone 160A) for each analytic request. In some embodiments, local dispatch may configure the analytic zone for an analytic request based on a plurality of commands included in the analytic request. In some embodiment, an analytic zone may be facilitated via containers or implemented within work zones (e.g., a virtual machine) in a cloud system.

For example, local dispatch 154A can be configured to create and configure an analytic zone 160A to execute a specific analytic request. To configure analytic zone 160A, local dispatch 154A may configure a compute environment 162A for the analytic request. Compute environment 162A may include an OS version or type, a minimum CPU capability, etc. as required in the operating requirements specified in the analytic request. Additionally, local dispatch 154A may install one or more software dependencies as specified in the analytic request. To configure analytic zone 160A, local dispatch 154A may configure storage 164A (e.g., minimum memory requirement) for the analytic request. In some embodiments, local dispatch 154A may configure data access 166A connections to one or more data sources stored in local datastore 170A as specified in the analytic request.

In some embodiments, upon completing execution of the analytic, local dispatch 154A can destroy analytic zone 160A. Further, local dispatch 154A can monitor a status of an analytic execution and provide the status back to user devices 130A-C via analytics controller 104.

FIG. 1B is a block diagram of a system 100B illustrating a distributed computational analytic sharing architecture, according to some embodiments. System 100B shows components that are described with respect to FIG. 1A. In contrast to system 100A, however, the distributed computational analytic sharing architecture of system 100B can be configured as a peer-to-peer system that does not require a central controller, such as analytics controller 104 of FIG. 1. In some embodiments, to enable peer-to-peer functionality, one or more of analytics nodes 140A-C can implement some or all of the functionality of analytics controller 104A, as described with respect to FIG. 1A.

For example, analytics node 140A of system 100B may include analytics processor 150A that implements the following components described with respect to analytics controller 104A: user enrollment 112, analytics enrollment 114, visualization 118, global dispatch 122, and logging component 124. Additionally, analytics processor 150A in system 100B may include user authentication 153A that is configured to implement the functionality of both user authentication 152A and user authentication 116, as described with respect to FIG. 1A. Additionally, analytics processor 150A in system 100B may include user interface 159A that is configured to implement the functionality of user interface 158A and user interface 120, as described with respect to FIG. 1A.

In some embodiments, memory 142A of system 100B may implement the functionality provided by one or more of the registries and repositories provided by analytics controller 104 of FIG. 1A. As shown in system 100B, memory 142A may include the following repositories implemented by analytics controller 104 of FIG. 1A: global analytics repository 108 and global results repository 110. In some embodiments, memory 142A includes external data source registry 147A that stores metadata of data sources located remotely from analytics node 140A. External data source registry 147A may operate similarly to internal data source registry 146A except the data sources specified in external data source registry 147A are not stored in local datastore 170A directly accessible by analytics node 140A. For example, these external data sources may be stored in local datastores 170B-C managed by respective analytics nodes 140B-C.

Figure 2A:
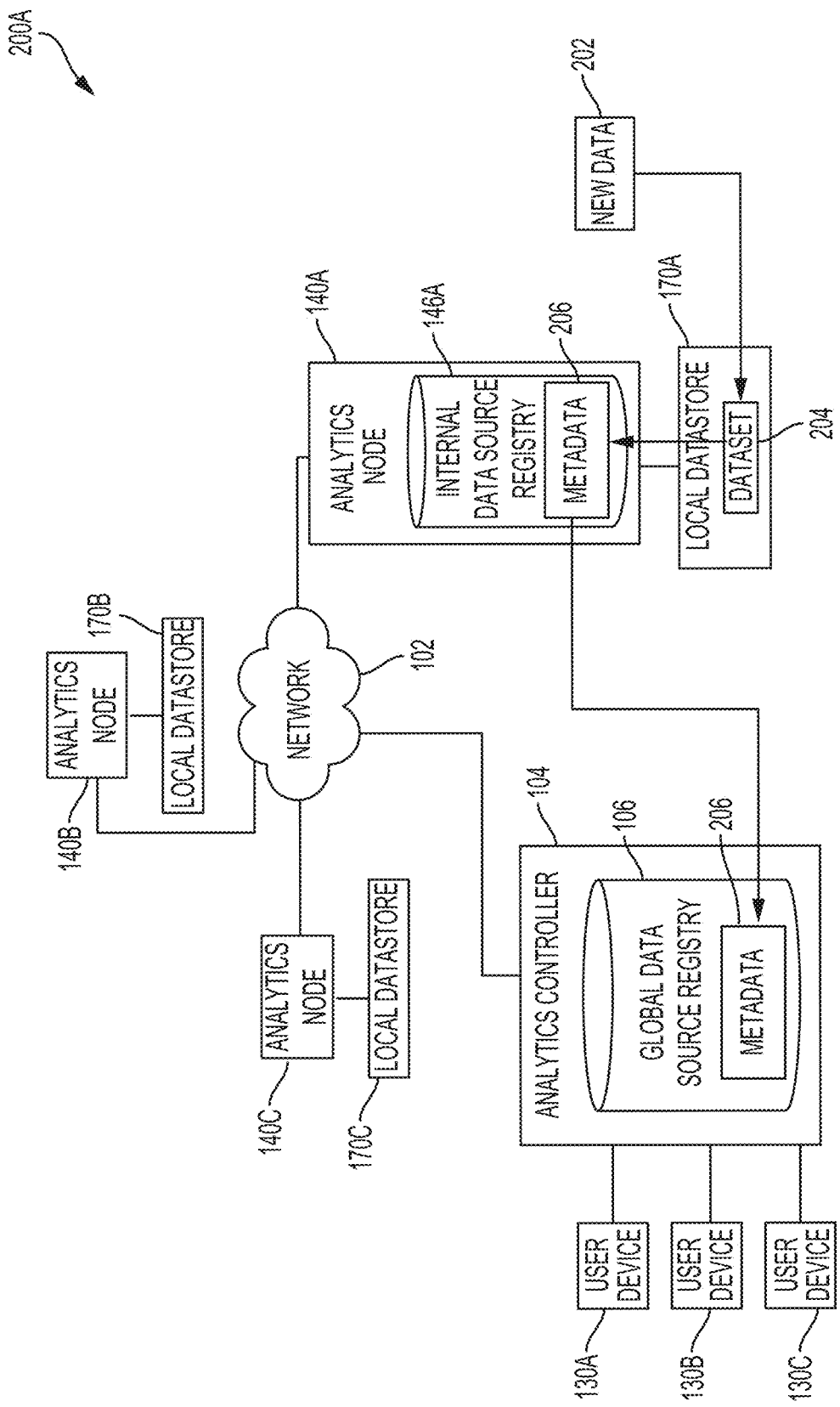
FIGS. 2A-C illustrate example data flows in a system that implements a distributed computational analytic sharing architecture, according to some embodiments.
Figure 2B:
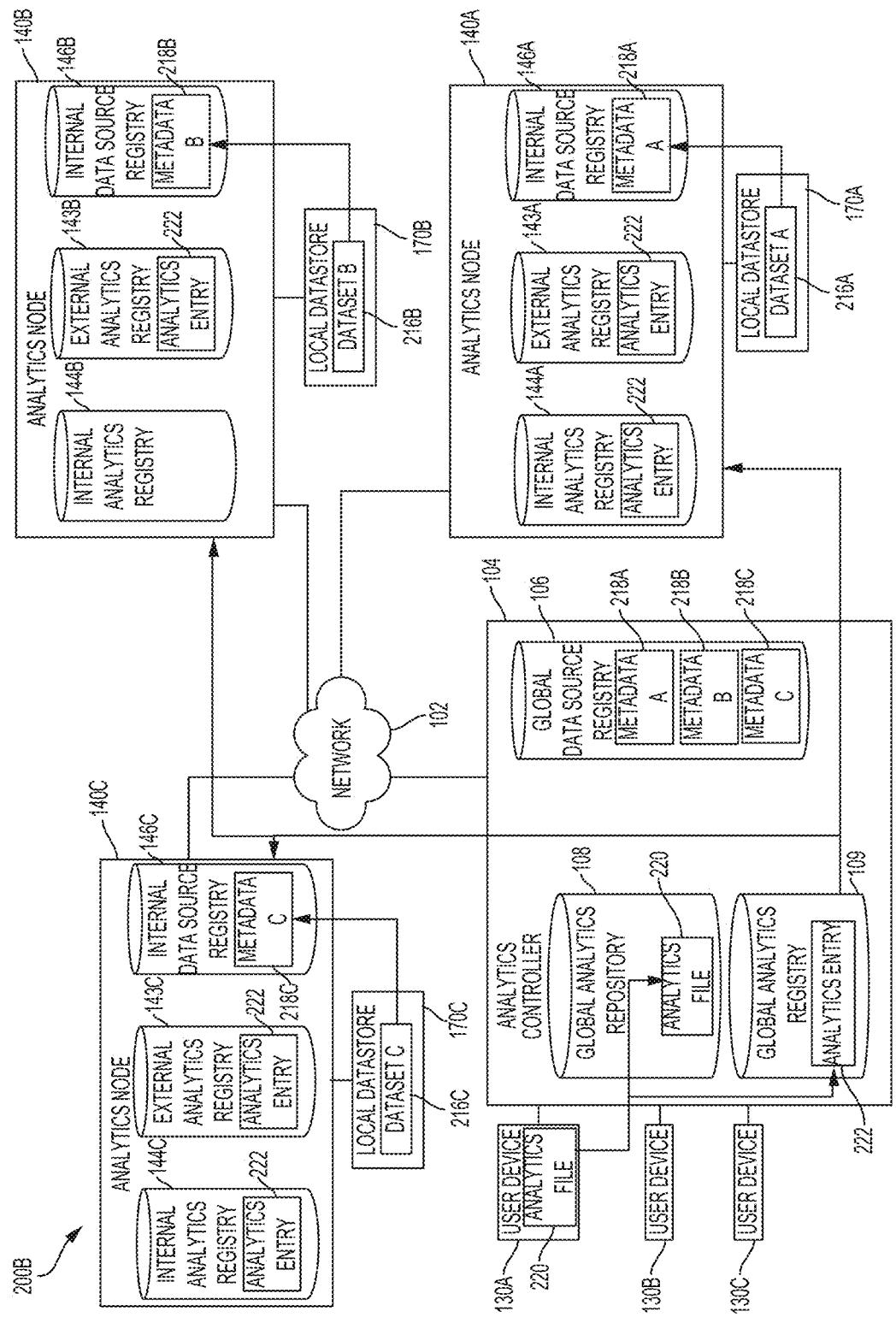
Figure 2C:
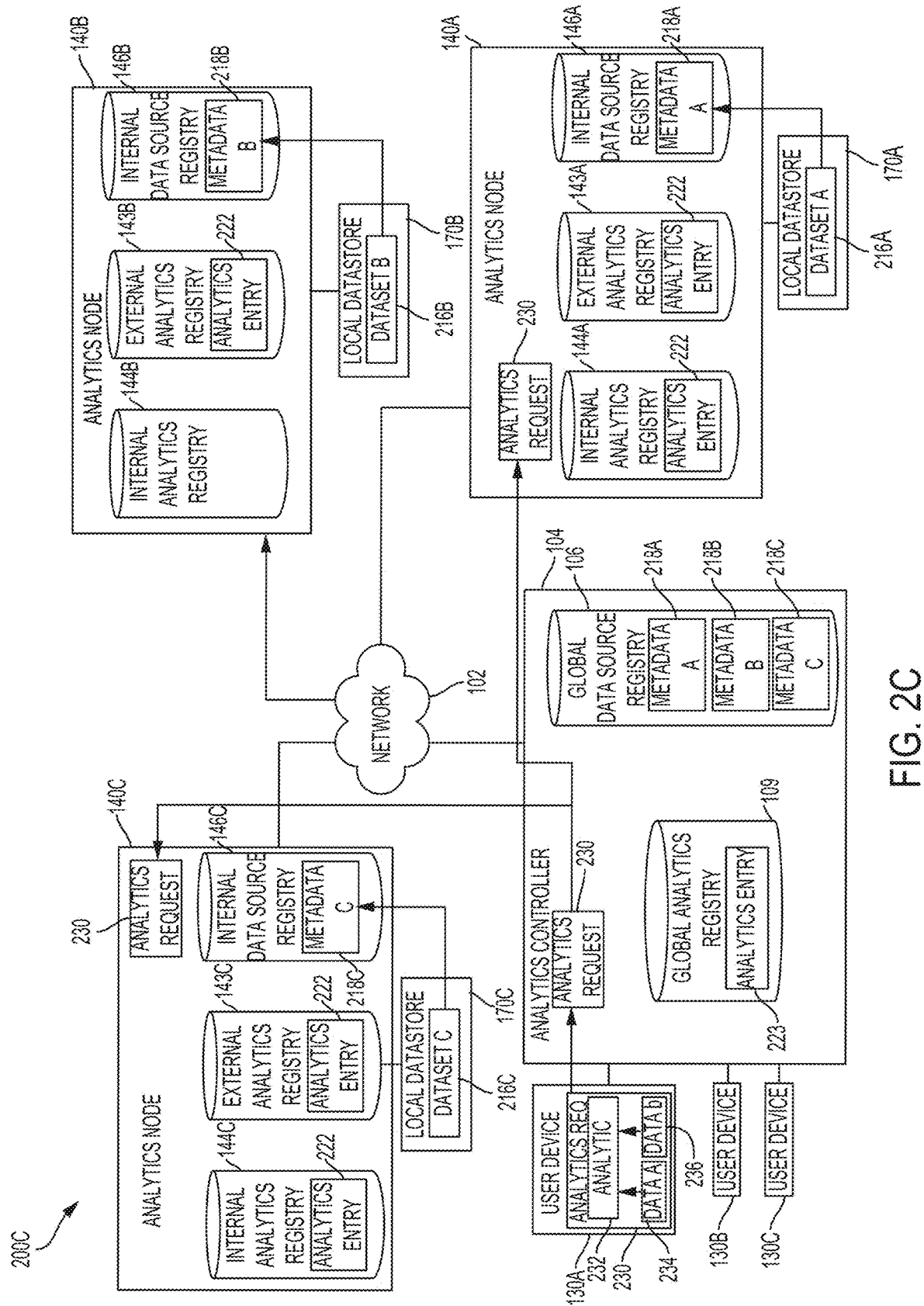

FIGS. 2A-C illustrate example data flows in a system that implements a distributed computational analytic sharing architecture, according to some embodiments.

FIG. 2A is a diagram 200A that illustrates how a new data source is added in the distributed computational analytic sharing architecture, according to some embodiments. Diagram 200A shows components that are described with respect to FIG. 1A. In some embodiments, a user may add new data 202 to be stored as dataset 204 in local datastore 170A managed by analytics node 140A. For example, new data 202 may be patient data related to an efficacy of a new drug. As described with respect to FIG. 1A, analytics node 140A can be configured to request the user to provide metadata 206 associated with dataset 204.

In response to receiving requested metadata 206, analytics node 140A can store metadata 206 as an entry in internal data source registry 146A. Then, analytics node 140A may be configured to generate a message indicating the update to internal data source registry 146A. As shown in diagram 200A, the message may be transmitted to analytics controller 104. Upon receiving the message, analytics controller 104 may store metadata 206 in global data source registry 106.

FIG. 2B is a diagram 200B that illustrates how a new analytic is added in the distributed computational analytic sharing architecture, according to some embodiments. Diagram 200B shows components that are described with respect to FIG. 1A. In some embodiments, each of local datastores 170A-C can store respective datasets 216A-C (labeled as dataset A, B, and C). Each internal data source registry 146A-C can be configured to store respective metadata 218A-C (labeled as metadata A-C) associated with corresponding datasets 216A-C. As shown in diagram 200B, global data source registry 106 stores metadata (i.e., metadata 218A-C) from each internal data source registry 146A-C.

In some embodiments, a user operating user device 130A may upload an analytics file 220 to analytics controller 104. In some embodiments, analytics controller 104 vets analytics file 220 against privacy and software security requirements before storing analytics file 220 in global analytics repository 108.

In some embodiments, analytics controller 104 prompts the user to input metadata and user access requirements associated with analytics file 220. Based on the received input, analytics controller 104 can be configured to store analytics entry 222 in global analytics registry 109. In some embodiments, analytics controller 104 can be configured to generate a message that indicates the update, i.e., analytics entry 222, to global analytics registry 109. The message may be transmitted by analytics controller 104 to one or more analytics nodes 140A-C via network 102.

In some embodiments, as will be described below with respect to FIGS. 4A-B, each of analytics nodes 140A-C that receives the message can be configured to determine whether analytics file 220 operates on one or more datasets stored locally with respect to the analytics node and whether the analytics node has the processing capability indicated in analytics entry 222. For example, each of analytics nodes 140A-C may store analytics entry 222 in respective external analytics registries 143A-C. Analytics node 140A may add analytics entry 222 to internal analytics registry 144A upon determining that analytics entry 222 includes input data types that match metadata 218A and analytics node 140A has the processing capacity specified in analytics entry 222. Similarly, analytics node 140C may add analytics entry 222 to internal analytics registry 144C upon determining that required inputs indicated in analytics entry 222 matches metadata 218C. In contrast, analytics node 140B may not store analytics entry 222 in internal analytics registry 144B. However, as shown in FIG. 2B, such analytics entry 222 may be stored in external analytics registry 143B representing the available analytics external to analytics node 140B. In some embodiments, by storing, within external analytics registry 143B, references to analytics that may be operated on data sources external to analytics node 140B, analytics node 140B may present a user with the option to issue an analytic request to the analytics nodes operating those external data sources.

FIG. 2C is a diagram 200C that illustrates how an analytic request is processed in the distributed computational analytic sharing architecture, according to some embodiments. Diagram 200C shows components that are described with respect to FIG. 1A and FIG. 2B.

In some embodiments, as will be further described below with respect to FIGS. 5A-B, a user operating user device 130A may generate analytic request 230. For example, upon receiving the user's selection to generate analytic request 230, analytics controller 104 may query global analytics registry 109 to provide the user with a plurality of analytics that the user is permitted to access. Then, the user may select one or more of the provided analytics, such as analytic 232 corresponding to analytics entry 223.

In some embodiments, upon receiving the user's selection of analytic 232 corresponding to analytics entry 223, analytics controller 104 may query global data source registry 106 to provide the user with one or more data sources compatible with the selected analytic 232. As described with respect to FIG. 2B, analytics entry 223 may be compatible with datasets corresponding to metadata 218A and 218C, in which case analytics controller 104 provides the user with an option to select one or both of the data sources corresponding to metadata 218A and 218C. As shown in diagram 200C, the user may have selected both data sources 234 and 236 corresponding to metadata 218A and 218C, respectively.

In some embodiments, once analytic request 230 is generated, analytics controller 104 can be configured to generate a message including analytic request 230. Then, analytics controller 104 may transmit the message to analytics nodes associated with the selected data sources 234 and 236. In the example shown, analytics controller 104 transmits the message to analytics nodes 140A and 140C. Each of analytics nodes 140A-C may independently vet analytic request 230 before executing analytic request, as will be further described below with respect to FIGS. 5A-C.

Figure 3A:
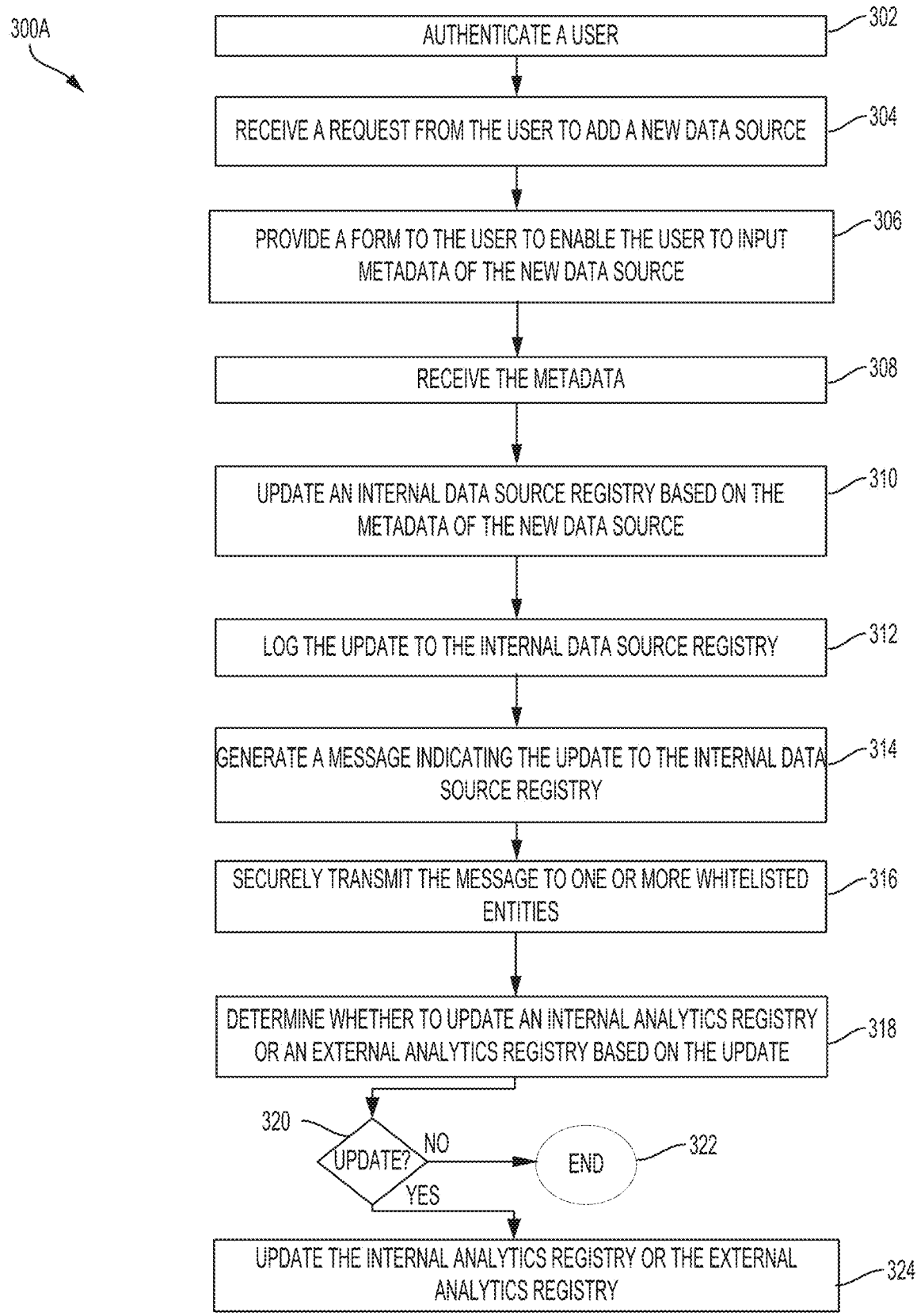
FIG. 3A illustrate a method that enables a user to add a new data source in a distributed computational analytic sharing architecture, according to some embodiments.
Figure 3B:
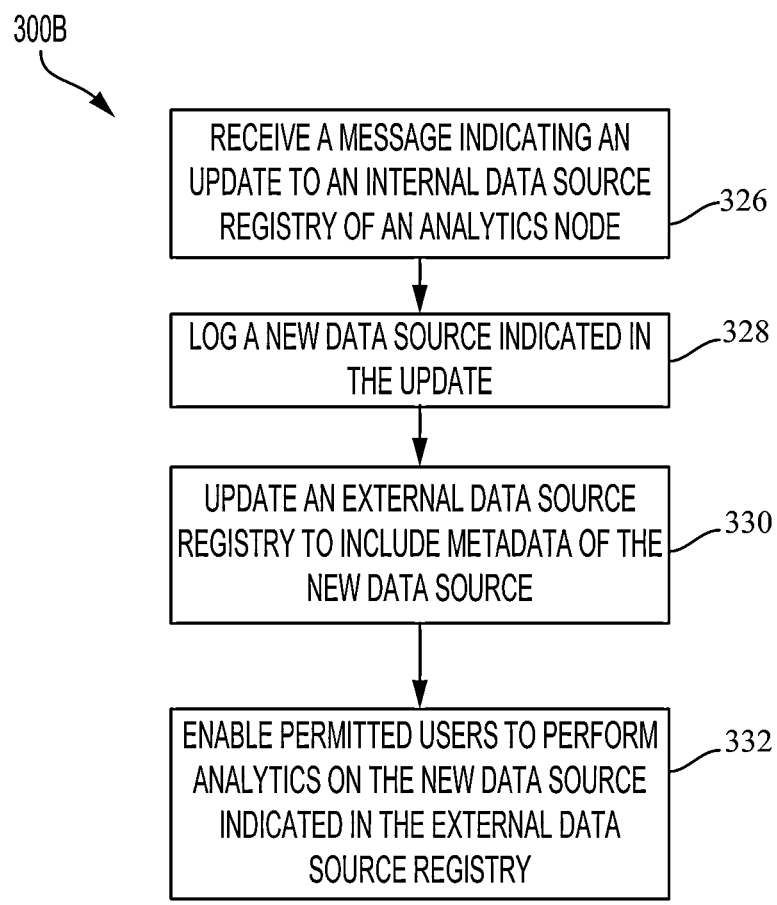
FIG. 3B illustrate a method that adds metadata of a new data source to enable users to access the new data source being remotely stored, according to some embodiments.

FIGS. 3A-B illustrate respective methods 300A and 300B that enable users to access data stored in a new data source, according to some embodiments. For example, users can run approved analytics on the data in the new data source. Each of methods 300A and 300B can be performed by a computing system with a processor and a memory (e.g., the computing system 600 illustrated in FIG. 6). Method 300A or 300B may be included in one or more programs stored in the memory that, when executed by the processor, cause the computing device to perform method 300A or 300B.

FIG. 3A illustrates a method 300A that enables a user to add a new data source in the distributed computational analytic sharing architecture, according to some embodiments. Method 300A may be performed by an analytics node, such as analytics node 140A from FIG. 1A. In some embodiments, the analytics node provides a user interface (e.g., user interface 158A) that enables the user to add the new data source.

In step 302, the analytics node authenticates the user before allowing the user the capability to add new data sources. For example, the analytics node may provide the user with a login webpage that requests the user to enter a username and a corresponding password. In some embodiments, the authentication can be performed by a user authentication component such as user authentication 152A of FIG. 1A.

In some embodiments, the analytics node may be configured to verify whether the authenticated user is permitted to add new data sources. For example, as part of authenticating the user, the analytics node may receive a user identifier (e.g., a username) that the analytics node uses to determine a corresponding user profile. The user profile may include the user's role and one or more privileges that specify whether the user is permitted to add new data sources. As described above with respect to user interface 158A of FIG. 1, the analytics node may graphically present the user with an option to add new data sources upon verifying the user's role or privileges permit such functionality.

In step 304, the analytics node receives a request from the user to add a new data source. In some embodiments, the new data source is stored on a local datastore, such as local datastore 170A of FIG. 1A, managed by the analytics node. In some embodiments, the analytics node presents a graphical user interface (e.g., through user interface 158A) that enables the user to select a graphical element to request addition of the new data source.

In step 306, in response to receiving the request of step 304, the analytics node (e.g., user interface 158A) provides a form to the user to enable the user to input metadata of the new data source. For example, the form may be a web form provided by user interface 158A to the user via a web browser. In some embodiments, before providing the form, the analytics node checks whether one or more data access rights (e.g., a credential) associated with the user permits the user to add the new data source. For example, in a hospital context, a credential that enables the user to add the new data source may be information indicating that the user is a hospital information technology (IT) administrator.

In some embodiments, the metadata of the new data source includes one or more of the following information: a name identifying the new data source, a short description of the new data source, one or more available data fields, a data format, a location indicator (e.g., a link or a file location) that specifies where the new data source is stored. In some embodiments, the metadata includes a data type of each of the one or more available data fields. In some embodiments, the metadata includes a plurality of filter options for a dataset stored in the new data source.

In some embodiments, the metadata includes data access requirements for the new data source that specify one or more data access rights that a user must possess to access the new data source. In some embodiments, the metadata includes data access requirements specific to each of the data fields of the new data source. In some embodiments, the data access requirements can be input by the user or assigned by the analytics node to the new data source or one or more data fields based on security policies stored at the analytics node.

In some embodiments, the metadata includes a list of whitelisted entities assigned by the user and indicating the entities that should be notified about the new data source. For example, a whitelisted entity may be an analytics controller or one or more analytics nodes.

In step 308, the analytics node receives the metadata inputted by the user in step 306.

In step 310, the analytics node updates an internal data source registry (e.g., internal data source registry 146A) based on the metadata of the new data source. In some embodiments, updating the internal data source registry includes adding an entry in the internal data source registry for the new data source. In some embodiments, the entry includes a plurality of fields to store different portions of the metadata. In effect, the internal data source registry may be configured as a catalog of the various data sources managed locally by the analytics node and stored in a local data store of the analytics node. The internal data source analytics registry enables the analytics node to locate requested data sources and perform approved analytics on data of requested data sources.

In step 312, the analytics node logs the update to the internal data source registry. In some embodiments, the log includes information specifying the new data source, the metadata of the new data source, the user who input the metadata, a timestamp for the update to the internal data source registry, or a combination thereof.

In step 314, the analytics node generates a message indicating the update to the internal data source registry. In some embodiments, the message includes the update. By indicating the update to the internal data source registry, the message may be transmitted to authorized parties to broadcast an availability of the new data source on which to run analytics.

In step 316, the analytics node securely transmits the message to one or more whitelisted entities included in the metadata. In some embodiments, the one or more whitelisted entities include the analytics controller. In some embodiments, the message can be securely transmitted in an email, an attachment of the email, in a VPN tunnel, or a combination thereof. In some embodiments, by communicating the availability of the new data source managed by the analytics node, the analytics controller can be configured to enable other users to request analytics to be performed on portions of the dataset stored in the new data source.

In step 318, the analytics node determines whether to update an internal analytics registry or an external analytics registry based on the update. In some embodiments, this determination includes whether one or more analytics specified in the internal analytics registry and the external analytics registry can operate on the new data source specified in the internal data source registry. For example, the analytics node may determine that a first analytic from the one or more analytics requires inputs compatible with the fields of the new data source.

In step 320, if an update to the internal analytics registry or the external analytics registry is determined, method 300A proceeds to step 324. Otherwise, method 300A proceeds to step 322.

In step 324, the analytics node updates the internal analytics registry or the external analytics registry, as determined in step 318. In some embodiments, the analytics node can update both the internal analytics registry and the external analytics registry. For example, a first analytic may be stored in the internal analytics registry to indicate that the analytics node can use the first analytic. The first analytic may also be stored in the external analytics registry if any of the other analytics nodes can also operate on the first analytic. In this example, the analytics node may determine that the first analytic is compatible with the new data source and update both the internal analytics registry and the external analytics registry.

In some embodiments, instead of implementing the distributed computational analytic sharing architecture as a centralized system, this architecture can be implemented as a peer-to-peer system. In the peer-to-peer implementation, the one or more whitelisted entities include one or more analytics nodes (e.g., analytics node 140B) approved by the user. Whitelist entries may be further refined to include one or more whitelisted users. In a peer-to-peer implementation, functionality of an analytics controller may be co-located with an analytics node at each site, as illustrated in FIG. 1B.

FIG. 3B illustrates a method 300B that adds metadata of a new data source to enable users to access the new data source being remotely stored, according to some embodiments. In some embodiments, method 300B may be performed by an analytics controller, such as analytics controller 104.

In step 326, the analytics controller receives a message indicating an update to an internal data source registry of an analytics node. For example, the message may correspond to the message transmitted in step 316 of method 300A. In some embodiments, as described with respect to method 300A, the message may include the update itself and include metadata of a new data source managed by the analytics node. In some embodiments, before further processing, the analytics controller can be configured to authenticate the received message using, for example, PKI.

In step 328, the analytics controller logs the new data source indicated in the update.

In step 330, the analytics controller updates an external data source registry to include the metadata of the new data source. In some embodiments, the analytics controller adds data access requirements to associate with the new data source or one or more data fields of the new data source such that only users with data access rights meeting the data access requirements are permitted to access the new data source or the one or more data fields of the new data source. Accordingly, analytics controller can be configured to manage an external data source registry that stores information about data sources managed by a plurality of analytics nodes and located remotely (and externally) with respect to the analytics controller.

In step 332, the analytics controller enables permitted users to perform analytics on the new data source indicated in the external data source registry. It is noted that the analytics controller may not have direct access to the new data source. As will be further described below with respect to FIGS. 5A-B, to enable a user to perform analytics on the new data source managed by the analytics node of step 332, the analytics controller can be configured to transmit an analytic request to the analytics node. In response to vetting and approving the analytic request, the analytics node can be configured to perform the analytic being requested on the new data source that it manages based on the internal data source registry stored at the analytics node.

FIGS. 4A-B illustrate respective methods 400A and 400B that enable users to access analytics to be run on data sources, according to some embodiments. For example, a first user can access an analytic generated by and uploaded by a second user. Each of methods 400A and 400B can be performed by a computing system with a processor and a memory (e.g., the computing system 600 illustrated in FIG. 6). Method 400A or 400B may be included in one or more programs stored in the memory that, when executed by the processor, cause the computing device to perform method 400A or 400B.

FIG. 4A illustrates a method 400A that enables a user to add an analytic to a distributed computational analytic sharing architecture, according to some embodiments. Method 400A may be performed by an analytics controller, such as analytics controller 104 from FIG. 1A, or an analytics node such as analytics node 140A. In some embodiments, the analytics controller provides a user interface (e.g., user interface 120) that enables the user to add the analytic. The analytics node may also provide a user interface (e.g. 158A) that enables the user to add the analytic locally. For example, if the analytics controller is remotely located, it may be more efficient for the user to complete the request locally through the analytics node, and then the analytics node will communicate the analytic add request to the analytics controller.

In step 402, an analytics controller authenticates the user before allowing the user the capability to add new analytics. For example, the analytics controller may provide the user with a login webpage that requests the user to enter a username and a corresponding password. In some embodiments, the authentication can be performed by a user authentication component such as user authentication 116 of FIG. 1A.

In some embodiments, the analytics node may be configured to verify whether the authenticated user is permitted to add new analytics. For example, as part of authenticating the user, the analytics node may receive a user identifier (e.g., a username) that the analytics node uses to determine a corresponding user profile. The user profile may include the user's role and one or more privileges that specify whether the user is permitted to add new analytics. As described above with respect to user interface 158A of FIG. 1, the analytics node may graphically present the user with an option to add new analytics upon verifying the user's role or privileges permit such functionality.

In step 404, the analytics controller receives a request from the user to add an analytic. In some embodiments, the analytics controller presents a graphical user interface (e.g., through user interface 120) that enables the user to select a graphical element to request addition of the analytic. In some embodiments, before providing the user with the graphical element, the analytics controller checks user access rights of the user to verify that the user is a privileged user allowed to upload new analytics.

In step 406, in response to receiving the request of step 404, the analytics controller (e.g., user interface 120) provides a form to the user to enable the user to input a functionality of the analytic and metadata of the analytic. For example, the form may be a web form provided by user interface 120 to the user via a web browser.

In some embodiments, the metadata of the analytic includes one or more of the following requested information: a name identifying the analytic, a short description of what the analytic does, one or more inputs and outputs of the analytic, metadata (e.g., a data type) of each of the one or more inputs and outputs, or a combination thereof. In some embodiments, the metadata includes processing resource requirements (e.g., minimum memory, CPU, or storage requirements, or a type of Operation System, etc.) and software dependency requirements (e.g., specific software packages such as MATLAB or links to open-source dependencies, etc.). The metadata may also include a pointer to a prebuilt, vetted virtual instance or container that already contains required dependencies.

In some embodiments, the functionality of the analytic can be one or more formulas or a series of calculations to be performed on one or more data variables. In some embodiments, the functionality of the analytic can be provided by the user in the form of uploading a source code file or an executable file. In some embodiments, the functionality of the analytic can be provided in the form of an analytics flow including two or more analytics stored in an analytics repository (e.g., global analytics repository 108) and referenced by an analytics registry (e.g., global analytics registry 109).

In step 408, the analytics controller receives the functionality and the metadata inputted in step 406.

In step 410, the analytics controller (e.g., analytics enrollment 114) vets the analytic against privacy and software security requirements based on the received functionality and the metadata. In some embodiments, the privacy and software security requirements are stored at the analytics controller. In some embodiments, vetting the analytic against software security requirements may include running anti-malware software on the source code or the executable file. In some embodiments, if the functionality is uploaded as an executable file, the analytics controller can be configured to run the executable file in a sandbox environment to determine whether the analytic includes malicious functions. In some embodiments, the analytics controller queues the analytic in a list of un-vetted analytics.

In step 412, the analytics controller determines whether the analytic is valid based on whether the analytic passes the check against the privacy and software security requirements. If the analytic is determined to be invalid, method 400A proceeds to step 414. Otherwise, method 400A proceeds to step 416.

In step 414, the analytics controller rejects the analytic requested by the user and logs a failure of vetting the analytic. In some embodiments, the analytics controller notifies the user of the rejection and one or more reasons while the analytic failed the check against privacy and software security requirements.

In step 416, in response to validating the analytic, the analytics controller prompts the user for user access requirements for accessing the functionality of the analytic. In some embodiments, the user access requirement may include one or more analytics nodes that can run the analytic or include one or more user access rights. The intention of the architecture is transparency regarding analytic function; therefore, proprietary aspects of any given analytic can be covered by copyright or patent in order to allow the architecture full visibility into the function of the analytic.

In step 418, the analytics controller receives the user access requirements inputted by the user. In step 420, the analytics controller updates an analytics registry (e.g., global analytics registry 109) based on the metadata of the analytic and the user access requirements. In some embodiments, updating the analytics registry includes adding an entry in the analytics registry for the analytic. In some embodiments, the entry includes a plurality of fields to store different portions of the metadata and the user access requirements for the analytic. In some embodiments, the functionality of the analytic can be stored in an analytics repository (e.g., global analytics repository 108) and the entry can include a location indicator specifying where the functionality of the analytic is stored in the analytics repository.

In step 422, the analytics controller logs the update to the analytics registry. In some embodiments, the log includes information specifying the analytic, the metadata and user access requirements of the analytic, the user who input the analytic, a timestamp for the update to the analytics registry, or a combination thereof.

In step 424, the analytics controller generates a message indicating the update to the analytics registry. In some embodiments, the message includes the update. By indicating the update to the analytics registry, the message may be transmitted to authorized parties to broadcast an availability of the analytic that has been vetted. In some embodiments, the message includes the functionality of the analytic. As described above with respect to step 408, the functionality of the analytic may be provided as a source code file or a set of visible instructions. In some embodiments, the functionality of the analytic can be provided in the form of an executable file. The intention of the architecture is transparency regarding analytic function; therefore, proprietary aspects of any given analytic can be covered by copyright or patent in order to allow the architecture full visibility into the function of the analytic.

In step 426, the analytics controller securely transmits the message to one or more whitelisted entities. In some embodiments, the one or more whitelisted entities include one or more analytics nodes (e.g., analytics nodes 140A-C). In some embodiments, the message can be securely transmitted in an email, an attachment of the email, in a VPN tunnel, or a combination thereof. In some embodiments, by communicating the availability of the analytic, other users that connect to whitelisted entities (e.g., analytics node 140A) can access the analytic to perform desired research.

FIG. 4B illustrates a method 400B for receiving and processing vetted analytics, according to some embodiments. In some embodiments, method 400B may be performed by an analytics node, such as analytics node 140A.

In step 430, the analytics node receives a message indicating an update to an analytics registry of an entity that generated the message. For example, the message may be generated by an analytics controller storing the analytics registry. In some embodiments, the message can correspond to the message transmitted in step 426 of method 400A. In some embodiments, as described with respect to method 400A, the message may include the update itself and include metadata of the analytic vetted by the entity. In some embodiments, before further processing, the analytics node can be configured to authenticate the received message using, for example, PKI.

In step 432, the analytics node logs the analytic indicated in the update.

In step 434, the analytics node updates an external analytics registry to include metadata of the analytic. In some embodiments, the message received in step 430 stores the metadata. In some embodiments, updating the external analytics registry includes adding an entry to the external analytics registry to specify the analytic. Basically, the external analytics registry can be configured to act as a catalog of analytics input by other users and vetted by the entity that generated the message as described in step 430.

In some embodiments, the message includes a file (e.g., a source code file or an executable file) specifying a functionality of the analytic. In these embodiments, the analytics node can be configured to store the file in an analytics repository (e.g., analytics repository 145A).

In step 436, the analytics node vets the analytic against privacy and software security requirements based on the received functionality and the metadata of the analytic stored in the message. In some embodiments, step 436 may correspond to step 410. However, the privacy and software security requirements of step 436 are specific to and stored on the analytics node.

In step 438, the analytics node determines whether the analytic is applicable to at least one data source indicated in an internal data source registry (e.g., internal data source registry 146A). In some embodiments, determining an applicability of the analytic includes determining that at least one data source includes data fields that match the input data parameters included in the metadata of the analytic. In some embodiments, determining an applicability of the analytic includes determining whether user access requirements of the data fields of the at least one data source is compatible with the user access requirements associated with the analytic.

In some embodiments, determining the applicability includes determining whether the analytics node has the software and hardware capability as required and indicated in the message.

In step 440, the analytics node determines whether the analytic is valid based on whether the analytic passes the check against the privacy and software security requirements of step 436 and whether the analytic is applicable to at least one data source as described in step 438. If the analytic is determined to be invalid, method 400B proceeds to step 442. Otherwise, method 400B proceeds to step 444.

In step 442, the analytics node rejects the analytic and logs a failure.

In step 444, in response to validating the analytic, the analytics node updates an internal analytics registry (e.g., internal analytics registry 144A) based on the metadata of the analytic and the user access requirements of the analytic. In some embodiments, updating the internal analytics registry includes adding an entry in the internal analytics registry for the analytic. In some embodiments, the entry includes a plurality of fields to store different portions of the metadata and the user access requirements for the analytic. In some embodiments, the functionality of the analytic can be stored in an analytics repository (e.g., analytics repository 145A) and the entry can include a location indicator specifying where the functionality of the analytic is stored in the analytics repository.

In step 446, the analytics node enables permitted users to request the analytic to be performed on the at least one data source, as will be further described below with respect to FIGS. 5A-B.

FIGS. 5A-B illustrate respective methods 500A and 500B that enable users to access shared analytics to perform distributed analytics on data sources, according to some embodiments. Each of methods 500A and 500B can be performed by a computing system with a processor and a memory (e.g., the computing system 600 illustrated in FIG. 6). Method 500A or 500B may be included in one or more programs stored in the memory that, when executed by the processor, cause the computing device to perform method 500A or 500B.

FIG. 5A illustrates a method 500A that enables a user to issue an analytic request in a distributed computational analytic sharing architecture, according to some embodiments. Method 500A may be performed by an analytics controller, such as analytics controller 104 from FIG. 1A. In some embodiments, the analytics controller provides a user interface (e.g., user interface 120) that enables the user to add and issue the analytic request.

In some embodiments, method 500A may be performed by an analytics node, such as analytics node 140A of FIG. 1B. Similarly, a user interface, such as user interface 159A, of the analytics node may facilitate the user's ability to add and issue the analytic request. In these embodiments, upon generating the analytic request, the analytics node may transmit the analytic request to an analytics controller, one or more analytics nodes, or a combination thereof.

In step 502, the analytics controller authenticates the user before allowing the user the capability to submit analytic requests.

In some embodiments, the analytics node may be configured to verify whether the authenticated user is permitted to submit analytic requests. For example, as part of authenticating the user, the analytics node may receive a user identifier (e.g., a username) that the analytics node uses to determine a corresponding user profile. The user profile may include the user's role and one or more privileges that specify whether the user is permitted to submit analytic requests. As described above with respect to user interface 158A of FIG. 1, the analytics node may graphically present the user with an option to submit analytic requests upon verifying the user's role or privileges permit such functionality.

In step 504, the analytics controller receives a request form the user to add an analytic request.

In step 506, the analytics controller provides the user with a list of analytics authorized for use by the user based on a query to an analytics registry.

In step 508, the analytics controller receives, from the user, a selection of an analytic from the list of analytics. In some embodiments, the selection of the user may include a plurality of analytics from the list of analytics.

In step 510, the analytics controller queries the analytics registry for metadata associated with the analytic to prompt the user with an option to enter input parameters indicated in the metadata. In some embodiments, the analytics controller can be configured to populate, within a user interface, a form with the analytics parameters retrieved from the analytics registry.

In step 512, the analytics controller receives one or more values for the input parameters entered by the user.

In step 514, the analytics controller queries a data registry for a list of data sources that are authorized for use by the user and that are compatible with the selection of the analytic. In some embodiments, the analytics controller prompts the user to select one or more data sources from the list of data sources.

In step 516, the analytics controller receives, from the user, a selection of one or more data sources from the list of data sources.

In step 518, the analytics controller queries the data registry for metadata associated with the selected one or more data sources to provide the user with an option to filter the data in the one or more data sources.

In step 520, the analytics controller receives data filter criteria entered by the user.

In step 522, the analytics controller generates the analytic request. In some embodiments, the analytics controller generates the analytic request based on the selection of the analytic, the selection of the one or more data sources, and the data filter criteria entered by the user.

In step 524, the analytics controller logs the analytic request.

In step 526, the analytics controller securely transmits the analytic request to one or more analytics nodes corresponding to the one or more data sources.

FIG. 5B illustrates a method 500B for receiving and processing an analytic request, according to some embodiments. Method 500B may be performed by an analytics node, such as analytics node 140A from FIG. 1A.

In step 530, the analytics node receives an analytic request. For example, the analytic request may be received from an analytics controller as described with respect to method 500A. In some embodiments, the received analytic request corresponds to the analytic request transmitted in step 526 of method 500A.

In step 532, the analytics node vets the analytic request. In some embodiments, the analytics node vets the analytic request against privacy and software security requirements stored at the analytics node. In some embodiments, the analytics node vets the analytic request by determining whether the analytics node has the processing capability to run the one or more analytics included in the analytic request. In some embodiments, the analytics node performs the vetting by querying an internal analytics registry (e.g., internal analytics registry 144A) for each of the analytics specified in the analytic request. If any of the analytics cannot be located in the internal analytics registry, the analytics node may determine that the analytic request cannot be executed. In some embodiments, vetting includes verifying that the user submitting the analytic request has permission to do so on this analytics node, and furthermore is permitted to run analysis against the data sources and data fields included in the analytic request.

In step 534, the analytics node logs the analytic request.

In step 536, the analytics node determines whether the analytic request is valid based on the vetting of step 532. If the analytic request is determined to be valid, method 500B proceeds to step 540. Otherwise, method 500B proceeds to step 538. In step 539, the analytics node denies the analytic request and logs the failure and may notify the user/submitter about the failure.

In step 541, the analytics node monitors a status of the analytic request. In some embodiments, the status may include queued for execution, currently being executed, or completed execution.

In step 540, the analytics node queues the analytic request for execution.

In step 542, the analytics node (e.g., local dispatch 154A) dispatches the analytic(s) request upon selecting the analytic request.

In step 544, the analytics node configures an analytic zone (e.g., analytic zone 160A) for executing the analytics. In some embodiments, the analytic request includes commands for configuring the analytic zone, as described with respect to FIG. 1A. In some embodiments, the analytics node configures the analytic zone with a computational environment (e.g., with a CPU capability, a specific OS version and type, etc.) and a memory (e.g., storage 164A) for executing the analytic request.

In step 546, the analytics node applies one or more software dependencies specified in the analytic request. In some embodiments, to determine which software dependencies to apply, the analytics node queries an internal analytics registry (e.g., internal analytics registry 144A) for one or more analytics specified in the analytic request.

In step 548, the analytics node installs the one or more analytics specified in the analytic request within the analytic zone. In some embodiments, the analytic request includes commands for installing the one or more analytics.

In step 550, the analytics node attaches one or more data sources specified in the analytic request to the analytic zone. In some embodiments, the node attaches to those data sources needed by the analytic (assuming permissions have already been vetted at this step) and specified in the analytic request. The analytics node may also copy the required data into the analytic zone to preclude the need to attach to unnecessary data sources or give access to unnecessary data fields.

In step 552, the analytics node executes the analytic request. In particular, the analytics node executes the one or more analytics specified in the analytic request on the one or more attached data sources. In some embodiments, the analytics node retrieves the one or more analytics to be installed from an analytics repository (e.g., analytics repository 145A).

In step 554, the analytics node stores a result of the execution of the analytic request to a results file. In step 556, the analytics node logs the result. In some embodiments, the analytic zone logs the result.

In step 558, the analytics node signals a completion of executing the analytic request. In some embodiments, the analytic zone signals the completion. In some embodiments, the analytics node subsequently updates a status of the analytic request to completion.

In step 562, the analytics node verifies that the result file includes permitted data.

In step 564, the analytics node determines whether the results are valid based on the verification performed in step 562. If the results are invalid, method 500B proceeds to step 566 and step 568. Otherwise, method 500B proceeds to step 570 and step 572.

In step 568, the analytics node sanitizes the data in the results by removing unpermitted data. In step 566, the analytics node logs a failure of the verification check of step 562.

In step 570, the analytics node logs a success of the verification check of step 562.

In step 572, the analytics node generates a message indicating an execution of the analytic request has been completed. In some embodiments, the message includes the result in the vetted results file. For example, the message may include a link to access the results or the contents of the results file may be included in the message body. In some embodiments, the results file can be included as an attachment to the message.

In step 574, the analytics node transmits the message to the analytics controller. In some embodiments, the message can be securely transmitted in an email, an attachment of the email, in a VPN tunnel, or a combination thereof.

Figure 6:
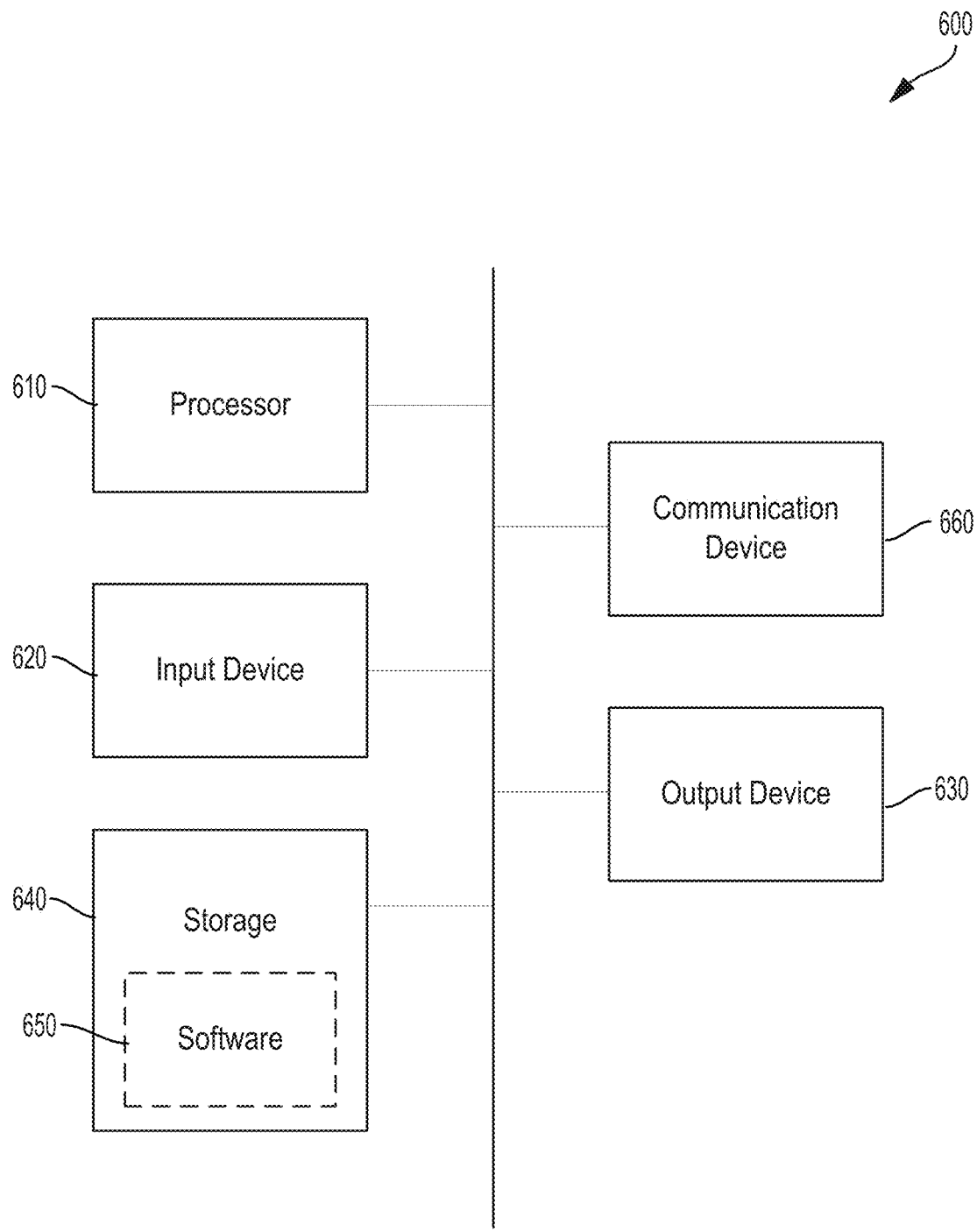
FIG. 6 illustrates an example of a computer in accordance with one embodiment.

FIG. 6 illustrates an example of a computer in accordance with one embodiment. Computer 600 can be a component of a system for implementing a distributed computational analytic sharing architecture according to the systems and methods described above, such as one of analytics nodes 140A-C or analytics controller 104 as described with respect to FIG. 1A. Computer 600 can also be a component of a system for implementing a peer-to-peer computational analytic sharing architecture according to the systems and methods described above as described with respect to FIG. 1B. In some embodiments, computer 600 is configured to execute each of methods 300A, 300B, 400A, 400B, 500A, and 500B of FIGS. 3A, 3B, 4A, 4B, 5A, and 5B, respectively.

Computer 600 can be a host computer connected to a network. Computer 600 can be a client computer or a server. As shown in FIG. 6, computer 600 can be any suitable type of microprocessor-based device, such as a personal computer, workstation, server, videogame console, or handheld computing device, such as a phone or tablet. The computer can include, for example, one or more of processor 610, input device 620, output device 630, storage 640, and communication device 660. Input device 620 and output device 630 can generally correspond to those described above and can either be connectable or integrated with the computer.

Input device 620 can be any suitable device that provides input, such as a touch screen or monitor, keyboard, mouse, or voice-recognition device. Output device 630 can be any suitable device that provides output, such as a touch screen, monitor, printer, disk drive, or speaker.

Storage 640 can be any suitable device that provides storage, such as an electrical, magnetic, or optical memory, including a RAM, cache, hard drive, CD-ROM drive, tape drive, or removable storage disk. Communication device 660 can include any suitable device capable of transmitting and receiving signals over a network, such as a network interface chip or card. The components of the computer can be connected in any suitable manner, such as via a physical bus or wirelessly. Storage 640 can be a non-transitory computer-readable storage medium comprising one or more programs, which, when executed by one or more processors, such as processor 610, cause the one or more processors to execute methods described herein, such as each of methods 300A, 300B, 400A, 400B, 500A, and 500B of FIGS. 3A, 3B, 4A, 4B, 5A, and 5B, respectively.

Software 650, which can be stored in storage 640 and executed by processor 610, can include, for example, the programming that embodies the functionality of the present disclosure (e.g., as embodied in the systems, computers, servers, and/or devices as described above). In some embodiments, software 650 can be implemented and executed on a combination of servers such as application servers and database servers.

Software 650, or part thereof, can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 600 can implement any operating system suitable for operating on the network. Software 650 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description sets forth exemplary methods, parameters and the like. It should be recognized, however, that such description is not intended as a limitation on the scope of the present disclosure but is instead provided as a description of exemplary embodiments. The illustrative embodiments described above are not intended to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. In the foregoing description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the foregoing description uses terms first, second, etc. to describe various elements, these elements should not be limited by the terms. These terms are only used to distinguish one element from another.

In addition, it is also to be understood that the singular forms "a," "an," and "the" used in the foregoing description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

In some embodiments, a non-transitory computer readable storage medium stores one or more programs configured to be executed by one or more processors of a computing device, the one or more programs including instructions for implementing any of the steps described or claimed herein. The present disclosure also relates to a device for performing the operations herein. This device may be specially constructed for the required purposes, or it may include a general purpose computer selectively activated or reconfigured by a computer program stored in the computer. Such a computer program may be stored in a non-transitory, computer readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referenced in this disclosure may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description above. In addition, the present disclosure is not described with reference to any particular programming language. It will be appreciated that a variety of programming languages may be used to implement the teachings of the present disclosure as described herein.

What is claimed is:

1. A method for securely distributing computational analysis across analytics nodes, comprising, at a first computing system implementing an analytics controller:

receiving a request from a user to issue an analytic request for requesting at least one analytic on pre-existing data;

providing the user with a plurality of analytics selected from an analytics registry of the first computing system based on matching a user privilege of the user with user access requirements of analytics in the analytics registry;

receiving, from the user, a selection of one or more analytics from the plurality of analytics;

providing the user with information pertaining to a plurality of data sources selected from a data source registry of the first computing system based on the selection of the one or more analytics and based on matching the user privilege with user access requirements of data sources in the data source registry, wherein the plurality of data sources comprise the pre-existing data stored at a plurality of external computing systems implementing a plurality of analytics nodes, the plurality of external computing systems being communicatively coupled via a communication network to the first computing system, wherein the information provided to the user comprises metadata associated with the plurality of data sources that is configured to specify types of data stored in each data source, wherein the metadata is configured to allow for the user to select from among the plurality of data sources without receiving the data stored in the plurality of data sources, and wherein the metadata is stored locally at the first computing system in a metadata repository that comprises metadata for the plurality of data sources;

receiving, from the user, a selection of one or more data sources from the plurality of data sources;

accessing a data converter repository that stores a plurality of data conversion functions to convert a dataset in the selected one or more data sources to a specific format required by the selected one or more analytics;

generating the analytic request, wherein the generated analytic request comprises the one or more analytics and the selected one or more data sources;

transmitting the analytic request via the communication network to one or more external computing systems implementing analytic nodes corresponding to the selected one or more data sources; and receiving a result from each of the one or more external computing systems implementing the analytics nodes corresponding to the selected one or more data sources, the result indicating a result of executing the analytic request on a selected data source managed by a corresponding external computing system implementing the analytics node corresponding to the selected data source.

2. The method of claim 1, comprising:
authenticating the user before providing the user with one or both of the plurality of analytics and the information pertaining to the plurality of data sources.

3. The method of claim 1, wherein receiving the selection of one or more analytics from the plurality of analytics comprises:
receiving an analytics flow combining two or more analytics selected from the plurality of analytics.

4. The method of claim 1, wherein providing the user with the information pertaining to the one or more data sources selected from the data source registry comprises:
querying the analytics registry based on the selection of one or more analytics to determine input data requirements to each of the one or more analytics; and
selecting each data source of the one or more data sources from the data source registry by matching the input data requirements with one or more data fields of each data source.

5. The method of claim 1, comprising:
querying the data source registry for metadata associated with the selected one or more data sources to provide the user with an option to filter the data in the one or more data sources;
receiving, from the user, data filter criteria entered by the user; and
adding the data filter criteria to the analytic request.

6. The method of claim 1, comprising:
encrypting the analytic request before transmitting; and
signing the analytic request with a private key.

7. The method of claim 1, wherein transmitting the analytic request one or more analytic nodes corresponding to the one or more data sources comprises:
for a first data source of the one or more data sources, querying the data source registry to identify a first analytics node of the at least one analytics nodes, wherein the first analytics node manages a local data store for storing the first data source.

8. A system for securely distributing computational analysis across analytics nodes, the system comprising an analytics controller, one or more processors, memory, and one or more programs stored in the memory and configured to be executed by the one or more processors, the one or more programs including instructions for:
receiving a request from a user to issue an analytic request for requesting at least one analytic on pre-existing data;
providing the user with a plurality of analytics selected from an analytics registry of the system based on matching a user privilege of the user with user access requirements of analytics in the analytics registry;
receiving, from the user, a selection of one or more analytics from the plurality of analytics;
providing the user with information pertaining to a plurality of data sources selected from a data source registry of the system based on the selection of the one or more analytics and based on matching the user privilege with user access requirements of data sources in the data source registry, wherein the plurality of data sources comprise the pre-existing data stored at a plurality of external computing systems implementing a plurality of analytics nodes, the plurality of external computing systems being communicatively coupled via a communication network to the system, wherein the information provided to the user comprises metadata associated with the plurality of data sources that is configured to specify types of data stored in each data source, wherein the metadata is configured to allow for the user to select from among the plurality of data sources without receiving the data stored in the plurality of data sources, and wherein the metadata is stored locally at the first computing system in a metadata repository that comprises metadata for the plurality of data sources;
receiving, from the user, a selection of one or more data sources from the plurality of data sources;
accessing a data converter repository that stores a plurality of data conversion functions to convert a dataset in the selected one or more data sources to a specific format required by the selected one or more analytics;
generating the analytic request, wherein the generated analytic request comprises the one or more analytics and the selected one or more data sources;
transmitting the analytic request via the communication network to one or more external computing systems implementing analytic nodes corresponding to the selected one or more data sources; and
receiving a result from each of the one or more external computing systems implementing the analytics nodes corresponding to the selected one or more data sources, the result indicating a result of executing the analytic request on a selected data source managed by a corresponding external computing system implementing the analytics node corresponding to the selected data source.

9. The system of claim 8, wherein the instructions comprise:
authenticating the user before providing the user with one or both of the plurality of analytics and the information pertaining to the plurality of data sources.

10. The system of claim 8, wherein receiving the selection of one or more analytics from the plurality of analytics comprises:
receiving an analytics flow combining two or more analytics selected from the plurality of analytics.

11. The system of claim 8, wherein providing the user with the information pertaining to the one or more data sources selected from the data source registry comprises:

querying the analytics registry based on the selection of one or more analytics to determine input data requirements to each of the one or more analytics; and selecting each data source of the one or more data sources from the data source registry by matching the input data requirements with one or more data fields of each data source.

12. The system of claim 8, wherein the instructions comprise:

querying the data source registry for metadata associated with the selected one or more data sources to provide the user with an option to filter the data in the one or more data sources;

receiving, from the user, data filter criteria entered by the user; and adding the data filter criteria to the analytic request.

13. The system of claim 8, wherein the instructions comprise:

encrypting the analytic request before transmitting; and signing the analytic request with a private key.

14. The system of claim 8, wherein transmitting the analytic request to one or more analytic nodes corresponding to the one or more data sources comprises:

for a first data source of the one or more data sources, querying the data source registry to identify a first analytics node of the at least one analytics nodes, wherein the first analytics node manages a local data store for storing the first data source.

15. The system of claim 8, wherein the system is a server.

16. The system of claim 8, wherein the system is a distributed cloud based system.

17. A non-transitory computer-readable storage medium comprising instructions for securely distributing computational analysis across analytics nodes, wherein the instructions, when executed at a first computing system implementing an analytics controller by a first cloud server having one or more processors, cause the one or more processors to perform instructions comprising:

receiving a request from a user to issue an analytic request for requesting at least one analytic on pre-existing data;

providing the user with a plurality of analytics selected from an analytics registry of the first computing system based on matching a user privilege of the user with user access requirements of analytics in the analytics registry;

receiving, from the user, a selection of one or more analytics from the plurality of analytics;

providing the user with information pertaining to a plurality of data sources selected from a data source registry of the first computing system based on the selection of the one or more analytics and based on matching the user privilege with user access requirements of data sources in the data source registry, wherein the plurality of data sources comprise the pre-existing data stored at a plurality of external computing systems implementing a plurality of analytics nodes, the plurality of external computing systems being communicatively coupled via a communication network to the first computing system, wherein the information provided to the user comprises metadata associated with the plurality of data sources that is configured to specify types of data stored in each data source, wherein the metadata is configured to allow for the user to select from among the plurality of data sources without receiving the data stored in the plurality of data sources, and wherein the metadata is stored locally at the first computing system in a metadata repository that comprises metadata for the plurality of data sources;

receiving, from the user, a selection of one or more data sources from the plurality of data sources;

accessing a data converter repository that stores a plurality of data conversion functions to convert a dataset in the selected one or more data sources to a specific format required by the selected one or more analytics;

generating the analytic request, wherein the generated analytic request comprises the one or more analytics and the selected one or more data sources;

transmitting the analytic request via the communication network to one or more external computing systems implementing analytic nodes corresponding to the selected one or more data sources; and receiving a result from each of the one or more external computing systems implementing the analytics nodes corresponding to the selected one or more data sources, the result indicating a result of executing the analytic request on a selected data source managed by a corresponding external computing system implementing the analytics node corresponding to the selected data source.

* * * * *